United States Patent
Szasz et al.

(10) Patent No.: US 9,937,357 B2
(45) Date of Patent: Apr. 10, 2018

(54) RF HYPERTHERMIA DEVICE FOR PERSONALIZED TREATMENT AND DIAGNOSIS

(71) Applicant: XAX KFT., Paty (HU)

(72) Inventors: Oliver Szasz, Paty (HU); Andras Szasz, Paty (HU); Nora Iluri, Los Gatos, CA (US)

(73) Assignee: XAX KFT., Paty (HU)

( * ) Notice: Subject to any disclaimer, the term of this patent is extended or adjusted under 35 U.S.C. 154(b) by 311 days.

(21) Appl. No.: 14/424,025

(22) PCT Filed: Aug. 27, 2013

(86) PCT No.: PCT/EP2013/067747
§ 371 (c)(1),
(2) Date: Feb. 25, 2015

(87) PCT Pub. No.: WO2014/033139
PCT Pub. Date: Mar. 6, 2014

(65) Prior Publication Data
US 2015/0217124 A1    Aug. 6, 2015

(30) Foreign Application Priority Data
Aug. 27, 2012 (EP) .................................... 12181833

(51) Int. Cl.
*A61B 5/05* (2006.01)
*A61N 1/40* (2006.01)
(Continued)

(52) U.S. Cl.
CPC ................ *A61N 1/403* (2013.01); *A61B 5/05* (2013.01); *A61B 5/483* (2013.01); *A61B 5/4836* (2013.01); *A61N 5/025* (2013.01)

(58) Field of Classification Search
CPC ...... A61N 1/403; A61N 5/025; A61B 5/4836; A61B 5/483; A61B 5/05
(Continued)

(56) References Cited

U.S. PATENT DOCUMENTS 4,712,559 A    12/1987  Turner
2005/0251234 A1*  11/2005  Kanzius ............. A61K 41/0052
607/101
(Continued)

FOREIGN PATENT DOCUMENTS

EP    1916013 A1    4/2008

OTHER PUBLICATIONS

Szasz et al. Radiofrequency hyperthermia device with target feedback signal modulation, Apr. 2010, wo2010/043372.*
(Continued)

*Primary Examiner* — Sanjay Cattungal
(74) *Attorney, Agent, or Firm* — Knobbe, Martens, Olson & Bear, LLP

(57) ABSTRACT

The present invention relates to a radiofrequency (RF) hyperthermia device for personalized treatment and diagnosis using capacitive coupling and without dipole antenna comprising a radiofrequency source, an amplifier, a sensor and a modulation signal input/generator, wherein the radiofrequency source produces a source signal which is modulated by the modulation signal input/generator using the phase information generated by homeostasis of the target to generate a modulated source signal, the modulated source signal is amplified by the amplifier and directed to a target, and the sensor detects the phase information generated by homeostasis of the target to provide a feedback signal, wherein the feedback signal modulates the source signal to generate a personalized modulated signal. This radiofrequency (RF) hyperthermia device is designed for personal-
(Continued)

ized treatment and diagnosis of a target such as a patient or a malignant or tumorous area within a patient.

12 Claims, 8 Drawing Sheets

(51) Int. Cl.
*A61N 5/02* (2006.01)
*A61B 5/00* (2006.01)
(58) Field of Classification Search
USPC .................................................. 600/407–480
See application file for complete search history.

(56) References Cited

U.S. PATENT DOCUMENTS

| 2006/0142748 | A1* | 6/2006 | Foreman | A61N 1/406 |
| | | | | 606/27 |
| 2006/0190063 | A1* | 8/2006 | Kanzius | A61N 1/406 |
| | | | | 607/101 |
| 2007/0250139 | A1* | 10/2007 | Kanzius | A61N 1/406 |
| | | | | 607/100 |
| 2009/0149799 | A1 | 6/2009 | Dacey, Jr. et al. | |
| 2011/0208182 | A1 | 8/2011 | Szasz et al. | |
| 2012/0065714 | A1* | 3/2012 | Szasz | A61B 18/1206 |
| | | | | 607/101 |

OTHER PUBLICATIONS

PCT International Search Report and Written Opinion of the International Searching Authority. dated Dec. 13, 2013, 14 pages.

\* cited by examiner

Figure 9
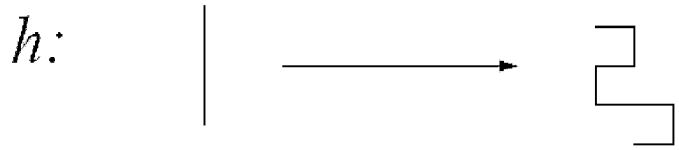
Figure 10
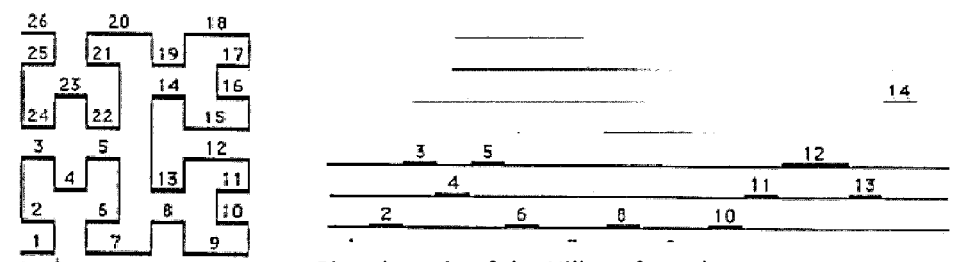
Part of Hilbert fractal     Pianola code of the Hilbert fractal
bejárása
Usual score of the pianola code above
Figure 11
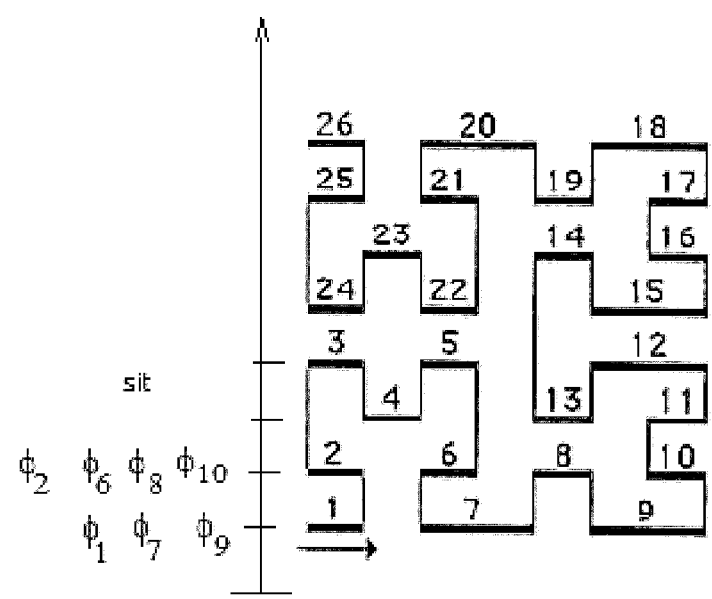

Figure 14
A
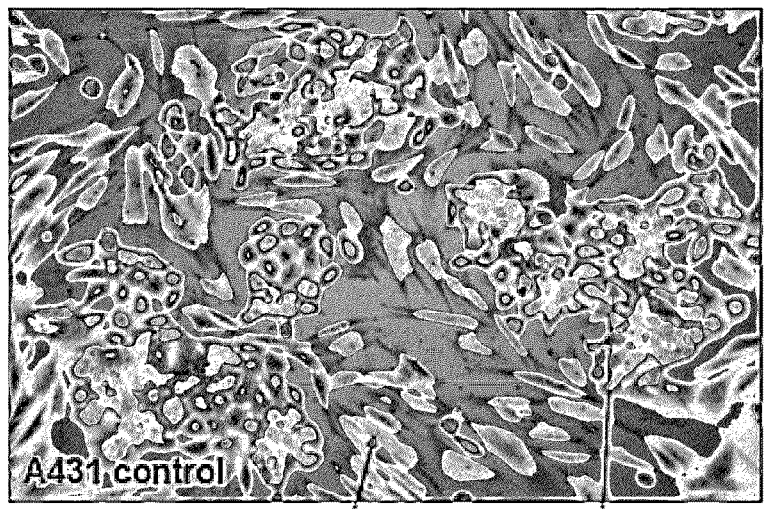
B
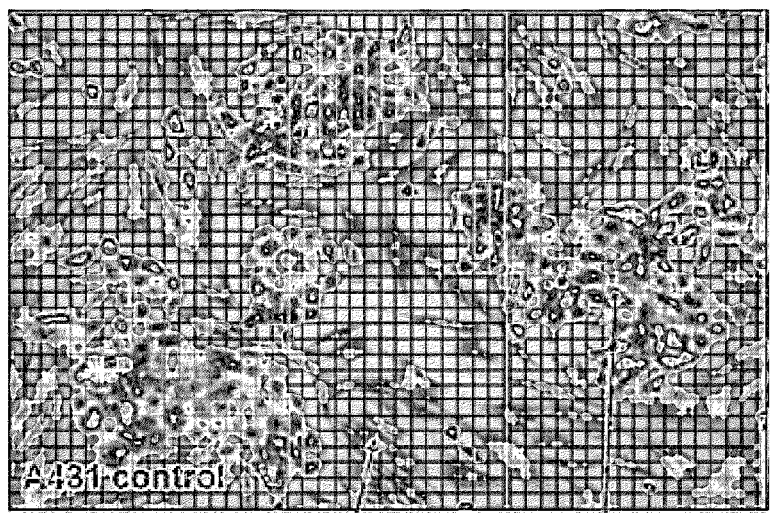

US 9,937,357 B2

RF HYPERTHERMIA DEVICE FOR PERSONALIZED TREATMENT AND DIAGNOSIS

The present invention relates to a radiofrequency (RF) hyperthermia device for personalized treatment and diagnosis using capacitive coupling and without dipole antenna comprising a radiofrequency source, an amplifier, a modulator, a sensor, and a modulation signal input/generator, wherein the radiofrequency source produces a source signal, which is modulated by the modulator using a modulation signal to generate a modulated source signal, the modulated source signal is amplified by the amplifier and directed to a target area, and the sensor detects the phase information generated by homeostasis of the target area and compares it with the previously obtained phase information to provide a feedback signal, wherein the modulation signal is generated by the modulation signal input/generator by modulating the feedback signal, said modulation signal input/generator being adapted to use the phase information of a measured homeostatic signal. This radiofrequency (RF) hyperthermia device is designed for personalized treatment and diagnosis of a target such as a patient or a malignant or tumorous area within a patient.

BACKGROUND OF THE INVENTION

Life is based on energetically open systems, where the environmental conditions determine it as equilibrium. The living equilibrium is the homeostasis. The actual homeostatic state is definitely "constant" despite its energetically open status. The normal healthy state of any living system is in homeostasis, which is not static, but dynamically changes in time, forming a relatively stable state. This relative stability makes it possible to recognize the various individuals despite the fact that millions of their cells actually vanish and millions of those are reborn. The homeostasis is controlled by numerous negative feedback loops, creating both the micro- and macro-structures in dynamic equilibrium. This "vibrating" equilibrium is controlled by oppositely effective physiologic feedback signal-pairs in various time-scales. This forms the actual state definitely "constant" despite its energetically open status (see FIG. 1). The system and its control are complex; they are not only simple sums of their subsystems.

Objective of the present invention is to provide an RF hyperthermia device for personalized treatment and diagnosis based on phase information obtained from homeostasis.

This objective is solved by the teaching of the independent claims. Further advantageous features and embodiments are evident from the description, the examples and the dependent claims.

DESCRIPTION OF THE INVENTION

The deterministic way of the control cannot be accurate and stable enough with appropriate processing velocity, thus the process is not deterministic. There is a crucial role of the random processes also to make the control optimal, not to use unnecessary accuracy and waste energy to control the system. The aims of the homeostasis are to safeguard the cellular functions and to assure the constant life-conditions for these smallest units. The environmental parameters must be kept in a tolerable band, the fluctuations of the actual values must not go over a definite limit for a longer time. These thresholds keep the average of the parameters constant in time, but due to the given band-width the deviation must also be fixed (see FIG. 2). The controlling physiological signals fluctuate around their average values. The feedback control is active above the acceptance and below the tolerance levels. The fluctuation is time-fractal, which characterizes the homeostasis. With the entropy considerations we show that the fluctuations are limited in the controlled range when the noise of the feedback signal is time-fractal.

To characterize the homeostatic equilibrium a special entropy-definition is herein introduced. There are various proposals to calculate the entropy of finite data-series, which are coherent with the Shannon-type entropy. Measuring complexity of time-series was introduced the Richman-Moorman-entropy. The Richman-Moorman-entropy is the negative logarithm of that conditional probability that the vectors remain r-neighbours, when we add a new sample-point to the time-series. Analyzing the multiple-scale entropy of physiological signals the Richman-Moorman-entropy was applied. Supposing that the Gauss-type pink-noise at physiologic signals is a good approximation due to the central limit theorem. The covariance matrix is necessary for characterizing the multidimensional Gauss-distribution. In case of the Gauss-pink-noise, the covariance matrix could be determined from the power spectrum, and on this basis the entropy as well.

Analysis proved the scale-independency of pink-noise in a definite interval of the signals. The multiscale entropy analysis (MSE) is applied to analyze various physiological signals. The entropy versus the applied scale factors (number of the members of the actual averaging) have different functions by applying pink- and white-noises. The smoothing (filtering, cutting the high-frequencies) is irrelevant in case of the pink-noise. When the original was pink, the entropy remains constant on all scales in a very wide range of limits. The entropy of the white-noise is decreased by the growing scale-factors, in consequence of the very short correlation; but its entropy is high at the scales, less than 4, due to the short range correlations. The short correlation is weak, but the long is strong for the pink-noise.

From physical point of view, the scaling of a discrete time series is a filtering process, which rejects some high-frequency components of the noise. The largest band-width of the noise is at scale 1. Gradually jumping onto a higher scaling, the average of the high-frequency components is more and the bandwidth decreases. The highest frequency in the signal could be estimated by the Shannon's sampling-theorem: the largest frequency appearing in the noise is the half of the sampling frequency. In consequence: in case of scale factor 2 the half, in case of scale factor n the n-th part of the highest frequency determines the bandwidth. The same is valid in the lowest frequency-limit of the bandwidth.

The length of the data-series is the function of the registration time. When $\Delta T$ is the sampling time and N is the size of the data-series, the time of registering is $\Delta TN$. The reciprocal value of this time is the smallest frequency in the signal, so it is the lower boundary of the bandwidth. Due to the decreasing length of the data-series by scaling, the lower frequency limit of the bandwidth is growing (see FIG. 3).

The Richman-Moorman-entropy of the time-series shows a "holographic-like" structure of the pink noise: the truncation of the noise does not change its entropy.

The Richman-Moorman-entropy of course has physical meaning in the same way as in the Shannon-entropy (they are coherent). Multiplying the Richman-Moorman-entropy by the Boltzmann constant, the physical entropy of the registered signal is constructed. The entropy of a system is the function of state; so it is a function of the state-variables, among which the energy is one of the most important variables. In our present case the energy of the system is the sum of the energy-values of the Fourier components of the registered noise. In consequence, the entropy of the signals formed from pink noise does not change by its decreasing energy. This case is seen in the thermodynamics: the entropy of the system in the equilibrium thermodynamics has extremum in function of energy, which means that the subsystems having thermodynamic equilibrium could exchange energies by fluctuations without changing the entropy of the system. It seems that a similar situation exists in case of such stochastic systems, which emit pink noise. If this analogy is valid, the subsystems can exchange considerable energy without changing the entropy of the system. Introducing a type of function like the temperature is impossible, because the entropy here isn't additive, as the entropies of all the pink-noise systems are equal. Here the entropy is more intensive than extensive parameter in the description of the system.

The mesenchyme has an important role of forming homeostasis in the organism. It is a loose connective tissue of an undifferentiated type. The pink-noise with entropy $S_E=1.8$ characterizes the homeostasis like an intensive parameter. This intensity is valid for every physiologic signal and for all the organs, the $S_E=1.8$ is a universal constant for the living body.

The cellular functions like supply and filtering are mediated by the mesenchyme, which represents a transmitter between the blood-capillaries and the cells. The mesenchyme is an ordered set of meshwork of connective species like highly polymerized hydro-carbonates, glycosaminoglycans, oligosaccharide chains connected to proteins, proteoglycans, and structure-glycoproteins, meshed by the dendrites of cellular glycocalix and by the extracellular matrix.

Mesenchyme has a trimodal function: cellular, humoral and neural. The cellular function brings the chemical equilibrium of connective tissue together with reticuloendothel cells. The humoral function controls the transport processes through the capillaries and lymph-network. This transport mechanism ensures the communication with far away systems. The neural function is responsible for the functional connection with all other parts of the organism. The three levels are different in their ranges: the cellular is local, the humoral is mesoscopic and the neural is global (systemic) interaction in the body. Due to the slow transport processes, the humoral effects are slow, while the neural is speedy.

The information control is effective by assistance of the neural system, of the cellular transport (hormones, enzymes, apoptosis, "social" signals) and of the humoral by blood and lymph transports too. The cell is the quickest to react. All the controlling mechanisms are operated by a pair of opposite signals: up- and down-regulation of the actual process. This is valid in all the time-scales having numerous pairs to form the physiological signals. The three levels are connected to each other by the mesenchyme.

The homeostasis is determined by the equilibrium of the large number of opposite pairs. As an example, we describe the proliferation homeostasis. There is a mechanism, which replaces the aged, harmed or too stressful cells. This process, which again the equilibrium of the opposite driving forces, stabilizes the final size of the organs. The opposite processes are the annihilation (apoptosis driven by the programmed cell death) and creation (cell division driven by growth factors). The two sides are in equilibrium in healthy state. When this equilibrium vanishes, the system cannot work well, that is the illness. When the apoptosis starts to dominate that could be an autoimmune disease, when the creation determines the process, the tumor is the result. The complexity of the system (which is characterized by the number of the opposing pairs) is the basic of the proper work, allows the system to accommodate properly to the environmental challenges. The acting signal-pairs are connected and coupled to each other, forming a unified complex system.

The above shown proliferation homeostasis works on the renewing of the cellular system, but one cell has to be annihilated giving place for the new-born one keeping the complete function in equilibrium (homeostasis). The equilibrium of this complex system could be described by fractal physiology and bio-scaling. This complexity is mirrored in the four dimensional description of the living state, which is valid in all scales of the life.

The complex network of the regulating pairs with opposite actions is the basis of the Traditional Chinese Medicine (TCM) and philosophy too (Yin-Yang pairs). The complexity means that the system cannot be simple additionally composed from their parts, the parts alone do not carry the function, which they have in the complete complex system. The couplings and interactions between the controlling pairs could explain the multi-functional behavior of tuning a single controlling pair, so the consequences of one external retuning of the balance could lead to various results.

We present this interaction of the sample of the proliferation homeostasis again. One of the functions of the mesenchyme is humoral by the transport of nutrients. When the oxygen supply is insufficient in an organ (hypoxia for example by the extreme utilization of a group of muscles), the conditions of the cells become hypoxic. The cells destroyed by the hypoxia release such chemicals into the extracellular electrolyte, which dissolve the endothelial cellular connections in the capillaries, breaking their adherent (cytoskeleton) connections. This ignites the first step of the angiogenesis, when the structure of the endothelial cells in the vessel-wall changes, the vascular tone reduces and the permeability of the vessel-wall increases. The increased permeability provides better oxygen and nutrient supply to the tissue. In the second stage of the angiogenesis protecolisenzymes evolve, making the extracellular electrolyte less viscose, giving possibility for the cells to have higher motility. The effect of the Vascular Endothelial Growth Factor (VEGF) is inducing cellular division and helping the chemotactically driven migration by the gradients of the growth factors. It starts building up a primitive network of vessels.

The fourth step of angiogenesis is the maturation, when the extracellular matrix is reconstructed, the cellular connections re-established, and the vessel-wall builds its stable final form. In this step the angiopoietin molecules have the duty to connect the primitive just-born capillarity vessels into the existing network. The proper physiological function (transport) of the new vessel is not enough to finish the job; transport must be given where the nutrient+oxygen supply is requested. The vessels are built up by a morphogenetic network, constructed by the gradients of the growth factors and by the electric potential gradients, which occur in the more negative daughter-cells than their matured counterpart (see FIG. 4.).

The potential gradient determines the direction of growth and the equilibrium is constructed by the dynamic control of the network of opposing pairs of actions, which is built up by the well determined scaling, ensure the proper equilibrium energy supply of the newly reborn complex system.

Consider that the environmental signal, which is controlled by a homeostatic process is an average of various components (see FIG. 5):

$$\langle x(t) \rangle = \frac{1}{n} \sum_{i=1}^{n} x_i \tag{1}$$

The average is the basic signal and the deviation form is the controlling error. Due to the random processes, the controlling error is a noise in the homeostasis.

Consequently, the noise is defined as follows:

$$z(t) = x(t) - \langle x(t) \rangle \tag{2}$$

wherein $\langle \ \rangle$ denotes the averaging by time. The variance of the noise $\langle z^2(t) \rangle$, is also time-dependent. Due to the living structure, the noise has to be self-similar. This means that the variance of the noise has a time-dependent power-function:

$$\langle z^2(t) \rangle = t^{2H} \tag{3}$$

wherein the similarity exponent is always positive: $0 < H$. Considering the following example as $H = \frac{1}{2}$, then the control-error variance is a linear function of the time:

$$\langle z^2(t) \rangle = ct \tag{4}$$

wherein c is constant. In this case, the error-signal is a Brownian-motion. The scaling law is in consequence of (3):

$$\langle z^2(rt) \rangle = r^{2H} \langle z^2(t) \rangle \tag{5}$$

The error signal can be characterized by the spectral power density function:

$$S(f) = F[G(\Delta t)] \tag{6}$$

wherein $G(\Delta t)$ is the autocorrelation function of the error signal:

$$G(\Delta t) = \langle z(t)z(t+\Delta t) \rangle - \langle z(t)^2 \rangle \tag{7}$$

The spectral power density function for the above introduces self-similar noises:

$$S(f) \propto \frac{1}{f^\beta} \tag{8}$$

The power $\beta$ is the "color" of the error signal and depends on H:

$$\beta = 2H + 1 \tag{9}$$

Consequently:

$$\beta \geq 1 \tag{10}$$

Hence if the error-signal is pink noise ($\beta = 1$, $1/f$-noise), then $$H = 0 \tag{11}$$

Therefore, due to (3), when the noise is $1/f$, then its deviation is constant in time in the well chosen interval. Indeed, the probability of the error signal exists in the interval $(\bar{x} - k\sigma, \bar{x} + k\sigma)$ (where $\sigma$ is the standard deviation) on the basis of the Chebishev inequality is:

$$P(|x - \bar{x}| < k\sigma) > 1 - \frac{1}{k^2} \tag{12}$$

Consequently, when the k is large enough, (large enough time is chosen for averaging) the probability is practically one, so the signal does not leave the chosen band. This means the system is well controlled in all times, the homeostasis is fixed, the system is regulated. The entropy of the system in this case is constant on all the scales ($S_E = 1.8$); the signals are controlled (they are kept in a definite interval) on all scales.

The structure of fluctuations is essential in this stochastic process. Time-fractal is the signal of stochastic control of homeostasis. When the power-spectrum of the error signal deviates from the pink-noise, thus having another color (for example $\beta > 1$), then its self-similar exponent will be positive, so according to (3) the deviation of the error-signal will grow in time, the homeostasis of the system will be broken. In these cases extra regulation (internal or external signals (e.g. immune reactions, transport-rearrangements, etc. or constrain treatments, therapies, etc.) is necessary to stabilize the system.

The mesenchyme is the coupling media of the action networks constructing the homeostasis. The mesenchyme is a crossing field of the homeostatic actions working like hubs for various and numerous actions. Modifying the hubs, the homeostatic control could be changed. Three main effects could act:

1. The mesenchyme over-controls. In this case the signal has to be down-regulated, purging is active.
2. When the signal is too low, it must be up-regulated, which is the tonization.
3. The signal is correct, but its deviation is too large, then a homeostatic entropy has to be produced at the hubs.

The actual local processes induced by the stimuli are not completely defined; however it is considered that the mechanical and electric factors make the disturbance, which promotes the natural correction system to re-establish the homeostatic equilibrium. Most probably various local disorders, like micro-wounds making injury current, like micro-bleeding inducing platelet-derived growth-factors (PDGF), like forced cellular apoptosis and replacing division, etc are complexly interacting and result in the re-establishment of the homeostatic equilibrium. Irrespective of the realized ways of the action, the acupuncture could give enough disturbance to rearrange the structure of the local hub to find the homeostatic equilibrium again by self-organizing way. This is much similar to the process when mechanical vibration is given to a bowl of cherries to arrange itself to a lower energy status with self-organization. The stimuli are active till the micro-disturbance exists. There are examples for the stochastic disturbance inducing self-organized processes in the bioprocesses.

Reforming the secondary, tertiary and quaternary structures of proteins operated by self-organizing way is one of the functions of stress-induced proteins (heat-shock proteins, HSP). HSP are providing such disturbances to the stress-unfolded parts, so that the molecules could find the lower energy state forming their normal structure again.

The dynamical fluctuations have pink-noise distribution, which ensures the equal deviation all over the system. The noise changes its character by disease or aging. The disease is the partial loss of the collectivity (the fluctuations are shifted towards the white noise, disordered), while the aging shifts the noise oppositely to the brown-direction (fixed routes, less adaptability, loss of complex adaptation facilities).

Aging

Aging decreases the complexity of the system. This loss means the degradation of the number of the opposite controlling pairs making the dialectic determinations. These changes could deviate the action time, the pairs act on different time-scales. Also we may assume that the quick action pairs are degraded first. All of these mean the aging is an MSE scaling, but the fluctuations of high frequency gradually disappear, the scaling possibility of the noise signal remains characteristic in normal aging cases, but shifts toward the Brownian noise ($1/f^2$). This corresponds to the $H=\frac{1}{2}$ in (3), so the variance becomes linearly growing by time, according to (4), the error-signal is a Brownian-motion, the aging suppresses the complexity, and the autocorrelation gradually decreases by time according to (7). The scaling is a good simulation of aging; the system gradually occupies larger scale-factors. The color of the noise of physiological signals can be studied to check the healthy state. Thus, the disease can be distinguished as the signal-noise is gradually shifted to white one and the correlation length decreases. On this way the loss of complexity by natural aging shifts the noise towards Brownian, opposite to the disease. The aging is the degradation of the competing pairs of signals, decreasing the complexity of the organism. This way, the color of the noise gradually changes to brown. A special scaling process occurs during the aging: the exponent of the frequency dependence of the power density function grows in this process from 1 to 2, but the homeostasis of the system is unchanged.

Disease—Cancer

The disease breaks the relative equilibrium, risks the relative stability of the system. The system tries to re-establish the homeostasis by enhancing the negative feedback control. The physiology tries to compensate and correct the damage. The system enhances the negative feedback controls enforcing the normalization (see FIG. 6).

Cancer is a disease of the loss of the collective control over a part of the cellular system, cells became individually autonomic. This state differs definitely from healthy one by its metabolic dominances, which was observed and honored by Nobel-price for Otto Warburg. According to Warburg's main idea, the primary cause of cancer is the non-oxidative glucose metabolism. The oxidative metabolism is the task of the mitochondria. Thus, the missing oxidative metabolism is a dysfunction of the mitochondria. According to Warburg, the mutation of the genome is a consequence of the fermentative metabolism: the hypoxia causes malignant transformation. His idea has been revised, and "returns in a New Theory of Cancer", and new hypotheses are formulated on this basis. The tumor metabolism and its mitochondrial connection is under intensive investigation.

The decisional role of the two metabolic pathways (the oxidative and the fermentative) was studied by Szent-Gyorgyi, having etiology approach, and using other formulation. His interpretation describes the cellular states by two different stages. The alpha-state of the cell is the fermentative status. This was general in the early development of the life, when free oxygen was not available. The aggressive electron acceptor was not present. In this stage only simple, primitive life forms could exist. The main task was to keep the life exist with their unlimited multiplication. This state was only reproduction oriented, so that the development of complex structures and complicated work-division was not possible. All the living objects in alpha state are autonomic, they are competing with each other, and cooperative communication does not exist between them. With the later presence of free oxygen beta-state of life was developed. The oxygen made possible to exchange higher value of electric charges, the unsaturated protein allowed more complex interactions, started the diversity of life. The cells in this state are cooperative, the task from the only multiplication became more complex, including the optimal energy consumption, the diversity for optimal adjustment to life. This is the phase, which had integrated the mitochondria for oxidative ATP production, and so produces the energy in high efficacy.

The alpha-state is the basic status of the life. In this state, the highest available entropy is accompanied with the lowest available free-energy. All complex living systems could easily be transformed into this basic state when became instable. Then, by the simple physical constrains (seek to low free energy and to high entropy) the cells try (at least partly) to realize the $\alpha$-state again. Again the system (or a part of it) contains cells with high autonomy and proliferation rate. By simple comparison the Szent-Gyorgyi's states and the Warburg's metabolic pathways are common: the alpha- and beta-states correspond to the fermentative and oxidative metabolism, respectively. With other words alpha-state prefers the host cell ATP production (anaerobic), while when the perfect mitochondria function works that is beta-state. These states are mixed (the cell works in both metabolic activity) and only a question of quantity their category. In normal homeostasis the $\beta$-state characteristics is about 70%. The actual balance fixes the actual status. The balance could be formulated by the cell status of co-operability (alpha$\leftrightarrows$beta); or formulated by metabolic ways (fermentation$\leftrightarrows$oxidation) or could be formulated with acting parts of metabolism: (host-cell$\leftrightarrows$mitochondrion). The meaning of all the formulations is equal: the actual energetic state is described. Note the interesting relation between the energy flux and co-operability. The high energy-flux makes the cells less cooperative and more primitive, while the low energy-flux makes the cells not only cooperative but also sophisticated, highly effective in energy production and in environmental adaptation as well.

Several modern approaches are developed in the last decades on the living complexity and its explanation. The basic categories of these are interconnected, and using description of the collectivity as self-organization, fractal physiology, and bioscaling. All of these models and descriptions are connected to the controlled energy combustion. The life has a control of the energy use, otherwise the chemicals have sudden and same-time reactions making explosion-like impulses instead of continuous energy-support of the system. The chemicals for energy liberation are transported to the reaction places by various methods, and so the transport properties define the energy balances. The metabolic activity has a scaling behavior in all the ranges of the living matter from the subcellular to the organism. The chemical reactions and the transport of reagents are the signal transductions, which are rather unified in all the living cells, so their scale-free networks are not surprising. All the reactions are surface controlled, so we expect an exponent for scaling by the mass $\frac{2}{3}$. The mass of the living object is volume dependent (scaling by 3), while the surface is scaled only by 2. However, the mass-dependent scaling of metabolism goes with $\frac{3}{4}$, like the life would be four dimensional. The bioscaling depends on the energy supply of the system, and so well describes the requested collectivity for healthy functions.

Based on scaling theory a general model for oncogenic growth was introduced, and discussed. All the healthy systems are collectively organized, which is broken by the cancerous processes. The cancer growth, at least at larger sizes, never happens among optimal nutrition supply, the cells are intensively competing for the available energy sources, they are individually acting, they are autonomic. It is clear from the cell culture experiments, where the metabolic rate does not depend on the cultured mass (has no scaling). It shows well: the scaling is a behavior of the cooperative, collective structures, and do not appear in the cases when the nutrition is available practically infinite due to the passage of the culture. This raises a question of the autonomy about the cancer cells. Probable, at the starting malignancy the situation corresponds with the infinite availability of nutrition for the "renegade" cell. However, by the growing number of "individuals" the nutrition starts to be limited. In this stage some cooperation features at least perish the weak or internal members of the "colony", appear. (Study the development of ant-colonies also supports this type of organization.) This was formulated theoretically and experimentally by the linear growth explained by the similarities with molecular beam epitaxy (MBE). The proliferation was observed highest on the free-surfaces, and the size of these determines the proliferative activity.

Therapy

Surprisingly it was found that the phase information obtained from homeostasis could be used to design a personalized treatment and diagnosis of a target such as a patient or a part of the patient's body in order to bring homeostasis again into a healthy equilibrium.

The differences between the therapies using common hyperthermia devices and the RF hyperthermia device of the present invention are as follows:

Common hyperthermia therapies use radiative coupling generated by an antenna arrangement, which simply produces heat in order to locally heat up the target. This is a local administration of heat normally under invasive conditions and the therapeutic effect is only obtained by the produced heat of the RF current.

In contrast the RF hyperthermia therapy of the present invention uses conductive coupling in a condenser arrangement, uses lower frequencies and obtains phase information, i.e. phase-codes providing information on the homeostasis of the target, thus enabling the inventive RF hyperthermia device to apply modulated RF signals in order to bring the homeostasis of the target again into a healthy equilibrium. Thus, in function of the stage of homeostasis of the target the inventive RF hyperthermia therapy makes a personalized treatment possible in the basis of phase information of homeostasis of the target such as a patient or areas of the patient such as organs or body parts or body regions of the patient.

The term "target" as used herein refers to the object (i.e. patient, human or animal) treated with the radiofrequency hyperthermia device according to the present invention. Thus the preferred target is a mammal, and even more preferred a human being.

The term "target area" or "load" as used herein refers to the body part of the target, which is exposed to the radiofrequency waves. As, the administration of the radiofrequency waves using the inventive radiofrequency hyperthermia device has the advantage of not being invasive, the "target area" or "load" corresponds to the body part of the target located between the electrodes or more specific between the electrodes of the condenser arrangement. This body part comprises the target area i.e. it comprises the malignant, diseased or painful area or tissue or cell, but also the healthy tissue and the healthy cells. However the healthy tissue and the healthy cells are not affected by the radiofrequency waves administered with the present inventive device.

The term "target tissue" refers to the malignant, diseased or painful tissue or cells. Thus the "target area" or "load" is the body part of patient located between the electrodes and exposed to the radiofrequency waves.

The effective therapy has to fit to the homeostatic control and has to be helpful for the complex feedback loops. It must help the body's internal corrective actions to re-establish the healthy state. Recognizing the disease, most of the medical approaches act with changes of the conditions (diets, medicines, other supplies) trying to constrain the body back to the previously working equilibrium.

However, in many cases the actually applied therapies in accordance with the present invention include constrains, which work against the natural homeostasis. The living organism starts to fight against the applied constraints together with the fight against the disease. For example: the classical hyperthermia, which introduces a new constrained effect, the heating out from the natural homeostasis. This constraint induces physiological feedback, forcing the body to fight on "double front": against the disease and against the action of the heat.

Recognizing the disease we act with our medical knowledge, and in many cases, we work against the natural homeostasis, the constrained action induces new homeostatic negative feedback. The body starts to fight against our constraints together with the disease (see FIG. 7). This controversial situation happens with classical hyperthermia, when the constrained massive temperature change is physiologically down-regulated (or at least the physiology works against it by the systemic [like blood-flow] and local [like HSP expression] reactions).

The treatment (referred to herein as "oncothermia") in accordance with the present invention disclaims the old approach, introducing a new paradigm: with the application of micro-heating induces considerably less physiological feedback to work against the action, and with the application of the electric field it uses such effect, for which the body has no physiological answer. With this new paradigm, oncothermia helps the natural feedback mechanisms to reestablish the healthy state (see FIG. 8).

The cellular alpha- and beta-states differ from electric point of view, and so the appropriately applied electromagnetic effects could change the states, pushing the balance to one or other dynamic state. This type of improving the actual treatment efficacy has been recognized in photodynamic processes.

In normal healthy state the body is in homeostasis. The natural therapy must help the body's internal corrective actions to re-establish the healthy state. We have shown that the entropy of every signal in this state is identical and constant: $S_E=1.8$. In the state of homeostasis the fluctuations of the control signals remain in a definite band showing time-fractal pattern in healthy organisms. The aging or stress processes cut the high-frequency parts and move the fractal exponent to higher values.

All the treatments must be active on the homeostatic control and consequently it has to be personalized by using the personal homeostatic equilibrium as the individual behaviour of the given person. The homeostatic control actually has a time-fractal fluctuation in all the organized organisms (the time-fractal is usually 1/f pink noise by its power density function) ensures the controlling limits of the fluctuation in all over the system in over wide frequency ranges.

The most important time-fractal fluctuation is the pink (1/f) noise, which is the character of the healthy control. All the healthy homeostasis has such fluctuation, but is does not mean that all the controls are the same. A simple example is, that analysis of all harmonic pieces of music results in a pink-noise, but they are so different by their actual sounds. The music is not a simple 1/f noise. It is a complicated (complex) time-space structure; a simple description does not exist. However, the music can be characterized by a few well-recognizable motives, (template-like structures). The 1/f spectrum is exactly the character of every musical piece, but the subsequent rank of the sounds is of course different. The templates built up from motifs are similar to the fractal construction in space. The physical realization of the music is a time-varying pressure field. It has some properties changing by definite rhythm, changing amplitude, time-interval, harmonics, prevalence and commonness of the frequencies and their groups. The power density spectra of such constructions are pink (1/f).

The professional composer can "hear" the music by simple imagination, not necessarily "hearing" the ear-transmitted senses. The sheet-music as a geometric fractal generates such brain processes, which are equivalent with the hearing of the same fractal-like music. Typical example the deft composer (like Beethoven was at the end of his life), whom the hearing itself was not necessary to "image" the music. The geometric fractal can generate the same images in the brain than the pink-noise pressure-fluctuation does in the membrane of the ear. However, not all the pink-noises generate pleasant feelings. Various senses (mainly the vision) could generate hallucinations, which are far from the objective content of the sensing. Such is for example the "flash-lag" effect, and some other optical illusions. A large number of hallucinations could be generated by noise only, for what the pink-noise is very effective. These 1/f-evoked brain processes are not from sensing of thinking. The human is able falling into trance, when the thinking, sensing, emotions are blocked. In this state very mixed, pleasant images can be generated without connections. This state is probable dominating the self-organized state all over the organism. The increased self-organizing noise is not sensible, because the internal systemic signals are out of the sensing possibilities. This self-organized noise must be out of normal sensing; otherwise, the outside signals could not be filtered form the overall noise background.

We proof in the followings that the addition a trivial energetic criterion to self-similarity gives the pink-noise power density spectrum. The self-similar function is f(t), then $$f(\tau t) = \tau^k f(t) \quad (13)$$

Assuming the Finite Square-Integral:

$$0 < \int_{-\infty}^{\infty} |f(t)|^2 dt < \infty \quad (14)$$

which allows the complex functions too. This physically means the self-similar pairs in the search. This criterion anyway means that the energy of the signal is finite, which is a simple, realistic assumption for all the physical signals. The self-similar exponents of such signals is $k = -\frac{1}{2}$:

$$E := \int_{-\infty}^{\infty} |f(t)|^2 dt = \quad (15)$$

$$\tau \int_{-\infty}^{\infty} |f(\tau z)|^2 dz = \tau(\tau^k)^2 \int_{-\infty}^{\infty} |f(z)|^2 dz = \tau^{1+2k} \int_{-\infty}^{\infty} |f(z)|^2 dz =$$

$$\tau^{1+2k} E \rightarrow \tau^{1+2k} = 1 \rightarrow k = -\frac{1}{2},$$

wherein a substitution $t=\tau z$ was applied. This exponent characterizes the 1/f power-spectrum, because the Fourier integral of the self-similar functions is self similar:

$$Fo[f(t)] = X(j\omega) = \frac{B}{(j\omega)^{1+k}} = \frac{B}{(j\omega)^{\frac{1}{2}}} \quad (16)$$

and with the Wiener-Hincsin's (also known as Wiener-Khinchin) theorem:

$$\int_{-\infty}^{\infty} |f(t)|^2 dx = \int_{-\infty}^{\infty} X(j\omega) X^*(j\omega) d\omega = \int_{-\infty}^{\infty} \frac{BB^*}{\omega} d\omega \quad (17)$$

In cases of unlimited length stationer signals the finite energy can not be guaranteed. In these cases the average power is finite only:

$$0 < \lim_{T \to \infty} \frac{1}{T} \int_{-\frac{T}{2}}^{\frac{T}{2}} |f(t)|^2 dt < \infty \quad (18)$$

when the signals are stationer and ergiodic the correlation functions could be formed from the representations with the limit:

$$R(\tau) := \lim_{T \to \infty} \frac{1}{T} \int_{-\frac{T}{2}}^{\frac{T}{2}} f(t) f(t-\tau) dt \quad (19)$$

which due to the finite average power exists. In case of the representation with T length in time $f_T(t)$ $$f_{(T)}(t) = \begin{cases} f(t), & -\frac{T}{2} \le t \le \frac{T}{2} \\ 0, & \text{otherwise} \end{cases} \quad (20)$$

It is plausible that $$\lim_{T \to \infty} f_T(t) = f(t).$$

The Fourier transform of the T-length representation is:

$$X(j\omega, T) = \frac{1}{2\pi} \int_{-T/2}^{T/2} f(t) e^{j\omega t} dt \quad (21)$$

The $\Phi(\omega)$ average power density of the T-length representations seeks to the Fourier transformation of the autocorrelation function:

$$\Phi(\omega) = \lim_{T \to \infty} \pi \frac{X(j\omega, T) X^*(j\omega, T)}{T} = \frac{1}{2\pi} \int_{-\infty}^{\infty} R(\tau) e^{-j\omega t} dt \quad (22)$$

Vice versa, the inverse Fourier transform of the average power density is the autocorrelation function:

$$R(\tau) = \frac{1}{2\pi}\int_{-\infty}^{\infty}\Phi(\omega)e^{j\omega\tau}d\omega \quad (23)$$

Consequently the average power is the Wiener-Hincsin theorem on stochastic signals:

$$R(0) = \lim_{T\to\infty}\frac{1}{T}\int_{-T/2}^{T/2}(f(t))^2 dt = \frac{1}{2\pi}\int_{-\infty}^{\infty}\Phi(\omega)d\omega \quad (24)$$

Substituting $\omega = \tau\overline{\omega}$ into (24), we obtain:

$$R(0) = \frac{1}{2\pi}\int_{-\infty}^{\infty}\Phi(\omega)d\omega = \quad (25)$$
$$\tau\frac{1}{2\pi}\int_{-\infty}^{\infty}\Phi(\tau\varpi)d\varpi = \tau\tau^{\alpha}\frac{1}{2\pi}\int_{-\infty}^{\infty}\Phi(\varpi)d\varpi = \tau^{\alpha+1}R(0)$$

Consequently $\alpha = -1$.

When the power spectrum of the 1/f noise is $\Phi(\omega)$, then $$\Phi(\omega) = \frac{A^2}{\omega} = \frac{A}{\sqrt{\omega}}\frac{A^*}{\sqrt{\omega}} = \frac{|A|e^{j\phi(\omega)}}{\sqrt{\omega}}\frac{|A|e^{-j\phi(\omega)}}{\sqrt{\omega}} \quad (26)$$

Hence, the power-density spectrum is the product of the signal and its conjugate, the time-representation of the stochastic signal is:

$$f(t) = \text{inverseFourier}\left(\frac{|A|e^{j\phi(\omega)}}{\sqrt{\omega}}\right) \quad (27)$$

wherein $\varphi(\omega)$ is a arbitrary function could be both deterministic or stochastic (random). In the last case, the function could be characterized by its distribution function. When the stochastic process represented by the function is ergodic, then the function could be characterized by its correlation function or by the Fourier transform of its power-density spectrum. This is a subsequent substitution possibility assuming that the power-spectrum of $\varphi(\omega)$ is 1/f, and so on. The random variable could be only the $\varphi$ phase of the amplitude. In this meaning the 1/f signals are different in their $\varphi$ phase, which identifies the actual distribution. Due to fact that the phase $\varphi$ is the carrier of the information, its distribution is the important character of the biological effect, and so distribution of the phase is the parameter on which the treatment personalization is based on.

The Personalization

The homeostatic equilibrium set by the action-pairs multiple feedback processes in the complex system. The control in healthy case remains in a definite band of fluctuation. The power-density function of this fluctuation shows 1/f spectrum in ideal systems. The information however is "hidden" in the phase of the power-amplitudes. The phase-coded distributions are personalized and well distinguishable, but their power density function shows the same 1/f spectrum in all cases. The situation is the same as in the case of the music: the power-density function of all the musical pieces is 1/f pink-nose, but of course all the musical pieces have special character, they are definitely different from each other.

This technical teaching gives possibility to personalize the actual treatment. Also, observation of the changes of this phase-code gives a possibility to make predictive control on the actual individual. This phase information is the core of our present invention.

The treatment will be personalized (phase-coded) 1/f noise, which is applied as modulation on the various carriers (which could be any electromagnetic, mechanical or other signal).

The individual has unified (personalized) phase code, because its complete organism is controlled by this code from micro- to macro-processes. This physiological control is independent from the actual voluntary nervous control and has to be coded by the homeostasis of the actual complex system.

The actual phase-code could be calculated by the cross-correlation functions of the various homeostatic fluctuations. The phase-code of the actual individual is characteristic of its organism, and the signal taken in the healthy youth could be the reference of the development of the actual homeostatic status.

In case of disease, which could be treated by various carrier waves the phase-coded fractal modulation would be the help of the re-establishing the homeostatic control. One of the most studied and well explained 1/f fluctuation is the heart-beat R-R interval (R wave to R wave interval in ECG). The modulation of this personal fluctuation could be one of the easiest personalizations of the treatment information. The modulation especially applied in the inventive hyperthermia device, where the 13.56 MHz carrier frequency is amplitude modulated with the personalized noise, is a major aspect of the present invention. This personalization is connected to the fluctuation of the energy-source, due to the blood-flow delivers all the energy components to all parts of the organism.

Other signals are also possible. Well studied multiple signals have 1/f noise fluctuation, even the EEG or other electric signals from the body can be used. The best fluctuations however are those, which are independent from the voluntary status. The natural fluctuations of controls of organs, which can be measured by electric signals like ECG or EEG in REM-sleep could be good pattern to choose.

Some, more sophisticated methods could be chosen for the personalization. In case of cancer-treatments the homeostatic information could be taken from the healthy counterpart of the tumorous tissue. The 2D or 3D patterns of the tissue could be considered as a quasi-periodic pattern, having characteristic (average) distance between the cells and around of this value a special fluctuation can be observed. Thus, a pathological structure of a healthy tissue can be considered as a reference for the same organ tissue, which has cancer. Therefore, the healthy tissue fractal-structure can be transformed to the time-fractal structure. The transformation is similar to the Jacquard machine, or the old barrel organ, when the various points of the structure (punched band or barrel) are transformed to other structures or sound by corresponding sound of the various structural units. For example, a pattern structure like the one displayed in FIG. 14 A, can be transformed by putting a grid on it like displayed in FIG. 14 B, wherein the various colors (and shadows) of the grid are corresponding to different sound (frequencies), and by reading the image row-by-row in continuous manner in a fractal noise. This special fractal noise will be characteristic to the pattern structure, but transformed to time. Any structure could be made on such way, and could be used as homeostatic signal of the given tissue for a very personalized modulation.

Thus, the geometrical (space) fluctuation is the phase-pattern when it is converted to time-scale. This time-conversion in its simplest way when we fix a frequency for the characteristic space-distances, and the distance fluctuations are measured in transformed frequency range by linear or logarithmic (physiological projection) scale.

We can construct special artificial templates for time-fractal construction too. These are similarly built up as the space-fractals, and the result is always 1/f but with different phase-coding.

In similar lines with the generation of a signal starting from the morphology of a tissue, EMG and the signal of the membrane ion-channels could be also measured and used as homeostatic signals.

This method can be used for diagnosis also, recognising when the fluctuation has been deformed and loses the homeostatic limits of the control.

The power-spectrum itself does not characterize the noise; many of time-functions can lead to the same power-spectrum. However, these noises could differ in the phase of their Fourier-components, which have anyway equal amplitudes. In a special case of the deterministic time-function $t^{-1/2}$, the phase of the noise is synchronized, having 1/f spectrum. Here the phases of the amplitudes of the Fourier components are rigorously equal, the phase is "synchronized". Other special class of these noises, when the phases are deterministically, for example we generate them by a set of definite frequencies. The widest class when the phase is a random variable.

When we know the phase-function template of the 1/f noise, we can make the 1/f as used in the well-known fractal-music as well. For example construct a Koch or Hilbert fractal in space (FIG. 9). After a few recursive steps we have the sub-fractal part (see FIG. 10).

The discrete phase-function could be constructed easily (FIG. 11). The starting point and the scale of the fractal are arbitrary, and so the time-fractal could be also arbitrary.

The RF Hyperthermia Device

The present invention relates to a radiofrequency hyperthermia device for personalized treatment, personalized prophylaxis and personalized diagnosis using capacitive coupling comprising a radiofrequency source (1), an amplifier (2), a sensor (3), a modulator (9) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target area (17), and the sensor (3) detects the phase information generated by homeostasis of the target area (17) and compares the phase information with the previously obtained phase information to provide a feedback signal (5), wherein the modulation signal (12) is generated by the modulation signal input/generator (13) from the feedback signal (5) by modulating the feedback signal (5), wherein the modulation signal input/generator (13) is configured and/or adapted to use the phase information of the measured homeostatic signal (19).

In case the term "personalized" might be regarded as unclear, we can state that the present invention refers to a radiofrequency hyperthermia device for treatment, prophylaxis and diagnosis using capacitive coupling comprising a radiofrequency source (1), an amplifier (2), a sensor (3), a modulator (9) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target area (17), and the sensor (3) detects the phase information generated by homeostasis of the target area (17) and compares the phase information with the previously obtained phase information to provide a feedback signal (5), wherein the modulation signal (12) is generated by the modulation signal input/generator (13) from the feedback signal (5) by modulating the feedback signal (5), wherein the modulation signal input/generator (13) is configured and/or adapted to use the phase information of the measured homeostatic signal (19).

Hence, according to the present invention only modulation signal/input generator configured and/or adapted to use the phase information of a signal can be used. None of the state of the art radiofrequency hyperthermia devices has such a component which is able to use phase information of a signal or more precisely the phase-code of the phase of the power-amplitudes of the power-density function of the fluctuation of the homeostatic equilibrium of the target (17).

The term "previous" in the context of "previously obtained phase information" refers to the phase information detected by sensor (3) at a defined time interval before comparison of the phase information or to the average of several phase information detected at different specified time intervals before the comparison of the phase information or to the average of all phase information detected during the on-going treatment with the inventive radiofrequency hyperthermia device before comparison of the phase information. Thus the term "previously" refers to one phase information or a multiplicity of single phase information(s) or the averaged phase information of two or more or a multiplicity of single phase information(s) or all phase information(s) which were obtained or measured before the phase information, i.e. the current phase information with which the "previously obtained" phase information has to be compared.

The RF hyperthermia device of the present invention is without dipole antenna. In case the feedback signal (5) needs to be amplified, a feedback amplifier (6) for amplifying the feedback signal (5) can be used in the inventive device.

In case the feedback amplifier (6) is present, the present invention relates to a radiofrequency hyperthermia device for personalized treatment and diagnosis using capacitive coupling (and without dipole antenna) comprising a radiofrequency source (1), an amplifier (2), a sensor (3), a modulator (9), a feedback amplifier (6) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target (17), and the sensor (3) detects the phase information generated by homeostasis of the target (17) and compares the phase information with the previously obtained phase information to provide a feedback signal (5), wherein the modulation signal (12) is generated by the modulation signal input/generator (13) from the feedback signal (5) by modulating the feedback signal (5), wherein the modulation signal input/generator (13) is adapted to use the phase information of the measured homeostatic signal (19).

Moreover, the radiofrequency hyperthermia device according to the present invention may comprise a multiplicator (11) for fitting the modulation generated by the modulation signal input/generator (13) to the feedback signal (5). The multiplicator (11) is preferably located between the feedback amplifier (6) and the modulation signal input/generator (13). Some parts of the electronic controls could be combined or integrated together.

It is also possible to combine the function of two or more parts of the inventive RF hyperthermia device. For example, the modulation signal input/generator (13) and the feedback amplifier (6) can be combined so that amplification and modulation is performed by one part of the device. In such a case the modulation signal input/generator (13) could also amplify the feedback signal (5) and also modulate the feedback signal (5) in order to generate the modulation signal (12).

It is also possible, that the modulation signal input/generator (13), the multiplicator (11) and the amplifier (6) are combined in one part, so that the amplification of the feedback signal (5), the modulation of the signal (5), and the fitting of the modulation generated by the modulation signal input/generator (13) to the feedback signal (5) are performed by one part of the device.

The inventive RF hyperthermia device uses capacitive coupling between the electrodes and RF current, which also runs through the target or target tissue of the patient while the body part of the patient between the electrodes acts like a non-perfect dielectric material wherein the target tissue is heated by Joule heat ($Q=I^2R$) generated by conversion of the current flow through the target tissue into heat as well as by the potential difference used for an electric field effect. Selectivity of the generation of heat mostly within the target tissue or the diseased tissue and not the healthy tissue is achieved by using conductivity differences of the healthy tissue in regard to the diseased or target tissue. Moreover, phase information of the status of homeostasis can be obtained by using the conductivity differences of the healthy tissue in regard to the diseased or target tissue. The target tissue such as a malignant tumor tissue has a higher complex or overall conductivity than healthy tissue and consequently has a higher absorption rate of the current going through it in comparison to healthy or normal tissue so that the Joule heat is mostly generated when the current passes the target tissue.

In order to outline the differences of the inventive RF hyperthermia device in comparison to state of the art hyperthermia devices the following summary was prepared. A state of the art hyperthermia device is described, for example, in US 2004/0230263 A1. It differs, however, from the present invention in the following features: In the device of US 2004/0230263 A1 dipole antennas (radiative coupling) are used. Radiative RF is applied through the patient or more precisely through the target tissue by using absorbed RF radiation. In the radiative solution the target is independent from the circuit, the feedback is made by the standing-wave-ratio (SWR) only, which measures the reflected power in comparison to the forwarded. The device of the present invention does not use dipole antennas; the inventive device uses a condenser arrangement wherein the patient's body between the at least one electrode and at least one counter-electrode is the dielectric material, which is part of the conductive circuit. This enables a direct control of the target as a part of the circuit, and generates a more precise and accurate feedback for controlling the process. The present invention uses condenser electrodes (capacitive coupling) for the application of RF-current through the respective body cross section. The maximal absorbed power in the target is optimized by a special tuning process. This conventional device induces phase-shifted interference between the antennas and interference of their standing wave radiation in order to tune the focus on the desired area. The present invention uses conductivity differences of the respective tissues (e.g. malignant tumor tissue has a higher conductivity than healthy tissue), thus leading to an automatic selection of the focus and for obtaining the phase information on homeostasis. This has immediate consequences on expansible organs like the lung or the heart, or if the patient moves during a treatment session which may exceed one hour. While the focus in the conventional device remains at the spot on which it was focused before, independent from the actual position of the tumor, the present invention follows any movement of the target because the RF current automatically flows in the correct direction. In this conventional device the target is treated like an electrically independent object absorbing the radiated energy. The present invention uses the target as a part of the electric circuit, as a dielectric material of a condenser in a resonant circuit. Consequently, the heating process is carried out and controlled in a different fashion. This conventional device uses SAR (specific absorption rate) absorbed energy as the only heating mechanism for achieving a beneficial effect. The present invention uses Joule heat ($Q=I^2R$) by converting the current flow into heat as well as the potential difference for an electric field effect. The conventional device uses frequencies above 130 MHz and normally between 130 MHz and 2400 MHz, while the inventive device uses frequencies below between 10 kHz and 50 MHz, more preferably between 130 kHz and 42 MHz and most preferably the values 135.6 kHz±5%, 339 kHz±5%, 678 kHz±5%, 1.356 MHz±5%, 3.39 MHz±5%, 6.78 MHz±5%, 13.56 MHz±5%, 27.12 MHz±5%, and 40.68 MHz±5%.

This conventional device controls temperature only as a tool for reproducing and standardising the therapy. In contrast, the present invention uses the absorbed energy (J/kg) and the conductivity of the patient (S=1/R) for strict control of the therapy conditions. This conventional device implicitly assumes that the success of the therapy depends only on the heat effect relative to the achieved temperature. By such a method mainly necrosis is caused in the target tissue. The present invention, however, does not require achieving such high temperatures at which necrosis occurs because the field effect causes apoptosis at lower temperatures. Thus, the inventive device treats tumorous or malignant tissue, cancer, tumours and especially solid tumours by inducing and/or causing apoptosis while common devices using radiative coupling induce necrosis. The device of the present invention does not use radiative coupling and uses the patient and especially the tissue of the patient between the electrodes wherein said tissue comprises the diseased tissue or also called the target tissue as dielectric material or dielectricum as part of the electric circuit.

However, the most important difference to all known hyperthermia devices is the use of the phase information of the homeostasis in the target, wherein the phase information can be generated by the homeostasis of the target area and the phase information of a measured homeostatic signal. Thus, the present invention refers to a radiofrequency hyperthermia device for treatment, prophylaxis and diagnosis or for personalized treatment, personalized prophylaxis and personalized diagnosis using capacitive coupling comprising a radiofrequency source (1), an amplifier (2), a sensor (3), a modulator (9) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target area (17), and the sensor (3) is adapted to detect the changes of the phase-code of the phase of the power-amplitudes of the power-density function of the fluctuation of the homeostatic equilibrium of the target area (17) and compares this phase information with the previously obtained phase information to provide a feedback signal (5), wherein the modulation signal (12) is generated by the modulation signal input/generator (13) from the feedback signal (5) by modulating the feedback signal (5), wherein the modulation signal input/generator (13) is adapted to use the phase information of the measured homeostatic signal (19).

In other words the present invention relates to a radiofrequency hyperthermia device for treatment, prophylaxis and diagnosis or for personalized treatment, personalized prophylaxis and personalized diagnosis using capacitive coupling comprising a radiofrequency source (1), an amplifier (2), a sensor (3), a modulator (9) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target area (17), and the sensor (3) is adapted to use the difference in the phase-code of the phase of the power-amplitudes of the power-density function of the fluctuation of the homeostatic equilibrium of the target area (17) and compares this phase information with the previously obtained phase information to provide a feedback signal (5), wherein the modulation signal (12) is generated by the modulation signal input/ generator (13) from the feedback signal (5) by modulating the feedback signal (5), wherein the modulation signal input/generator (13) is adapted to use the phase information of the measured homeostatic signal (19).

However, it is also possible for the inventive device to be operated without a feedback amplifier (6) or without a modulation signal input/generator (13). This would result in a mixed spectrum modulation, which could be used and is used for applications other than tumour treatment, such as for pain management, disorders of the central nervous system and other disorders where the exchange of biological information between the cells and parts of the body is faulty. Pain killing by heat has been already observed by ancient doctors and can also be achieved by hyperthermia applications) and by an electric field (TENS effect). All the patients with tumor had experienced the pain killing of the treatment using the inventive device, and they report relaxed, convenient treatment time, in most of the cases they fall asleep during the one-hour treatment process.)

In contrast, no modulation is introduced in conventional devices. The aim in conventional hyperthermia is to reach the highest possible temperature and for that the source carrier frequency is enough.

The modulation of the source signal frequency (8) by the modulation signal (12), which is generated by the modulation signal input/generator (13) from the feedback signal (5) by modulating the feedback signal (5), wherein the modulation signal input/generator (13) is adapted to use the phase information of the measured homeostatic signal (19).

The additional information gained from the feedback signal (5) and the measured homeostatic signal (19) provides an information boost in comparison to the simple unselective power treatment. This information makes it possible to select and optimize the actual energy distribution and to render the actual energy delivered to the target tissue more effective. Consequently, the inventive hyperthermia device is able to selectively heat target tissue, which might be tumorous, cancerous, malignant, inflamed or otherwise from normal or healthy tissue distinguishable tissue. The inventive device does not unselectively heat a body area comprising both target tissue, and normal or healthy tissue without differentiation. Consequently, the modulation used within the present invention increases the target tissue specificity and consequently the selective generation of heat within the target tissue, while heating or unnecessary heating of the surrounding normal or healthy tissue can be avoided or vehemently reduced.

In the case of hyperthermia treatment of tumour tissue using conventional devices the power alone heats both healthy tissue and tumour tissue unselectively and heats all tissues according to the law of the absorption of electromagnetic waves of a given frequency, power and of course the target material. Thus, in classical hyperthermia the complete tissue is heated and success depends on the differing sensitivities of healthy tissue and tumour tissue to heat, while heating the healthy tissue around the tumour tissue supports tumour growth and proliferation of cancer cells due to the increased delivery of nutrients to the diseased tissue as a result of increased blood flow. Consequently, it is not desired to heat the healthy tissue in vicinity to the diseased and especially tumorous or cancerous tissue.

Thus, the present invention displays an important difference: The input energy carries information and is selective at least in synergy with the selective factors of the targeted cellular structures. Therefore, when using the inventive device focusing the energy onto a target tissue is not as important as it is in classical hyperthermia, because the inventive device provides for self-selection, i.e. a form of autofocusing.

Consequently, the present invention is also directed to a modulation feedback circuit comprising a feedback amplifier (6) for amplifying the feedback signal (5), preferably, but optionally a multiplicator (11) to provide a further modulated signal (12) to the modulator (9), a sensor (3) adapted to detect the phase information generated by homeostasis of the target area (17) and to compare said phase information with the previously obtained phase information, a modulation signal input/generator (13), which is configured and/or adapted to use the phase information of the measured homeostatic signal (19) and a modulator (9) for receiving a modulation signal (12), which was generated by the modulation signal input/generator (13) from the feedback signal (5) by modulating the feedback signal (5). Thus, the modulation signal (12) is generated by the modulation signal input/generator (13) from the feedback signal (5) by modulating the feedback signal (5).

This modulation feedback circuit is used for the manufacture of the inventive RF hyperthermia device useful for the treatment and after-treatment of tumors, cancer pain, migraine and diseases of the central nervous system as well as for the prophylaxis of pain, migraine, cancer formation, tumor formation and the development of diseases of the central nervous system.

The present invention is also directed to a RF hyperthermia device for (personalized) treatment, (personalized) prophylaxis and (personalized) diagnosis using capacitive coupling with conductive electrodes, forcing RF-current between them and without dipole antenna comprising a radiofrequency source (1), an amplifier (2), a modulator (9), a sensor (3), optionally a feedback amplifier (6) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target (17), and the sensor (3) detects the phase information generated by homeostasis of the target (17) and compares the phase information with the previously obtained phase information to provide a feedback signal (5) to the feedback amplifier (6) if present, wherein the feedback signal (5) is amplified by the feedback amplifier (6), if amplifying is necessary to generate a amplified feedback signal (7), wherein the modulation signal (12) is generated by the modulation signal input/generator (13) from the feedback signal (5) or the amplified feedback signal (7), by modulating the feedback signal (5) or the amplified signal (7), wherein the modulation signal input/generator (13) is adapted to use the phase information of the measured homeostatic signal (19).

Thus, the essential parts of the device are the radiofrequency source (1), the amplifier (2), the modulator (9), the sensor (3), and the modulation signal input/generator (13). Moreover, preferred is also the presence of a feedback amplifier (6), but this is not mandatory. All further parts are optional and not necessarily required but for certain embodiments preferred.

The inventive RF hyperthermia device will be described with reference to FIGS. 12 and 13. The numbering of the parts of the inventive RF hyperthermia device in the FIGS. 12 and 13 is as follows.

(1): a signal generator (oscillator—the radiofrequency source), which provides the selected frequency (preferably 13.56 MHz) by means of a fixed stable quartz-oscillator, (2): an amplifier (RF), which provides the necessary energy supply for the conduction heating wherein the tuner optimizes the conduction for the individual patient, (3): a feedback sensor (current/power) signal sampling unit (RF-current sensor), which controls the forwarded power of the source and the reflected power of the target, (4): an x(t)—amplified modulated signal (amplified target-modified signal), which is responsible for the treatment in the target tissue, (5): a feedback signal, which carries the information of the actual treatment in a complex form and contributes to its control, (6): a feedback amplifier, which amplifies the feedback signal up to the desired level for further use, (7): an amplified feedback signal, (8): a F(t)—carrier signal which is the power RF-signal (preferably at 13.56 MHz) corresponding to the amplitude modulated by the modulator (9), (9): a modulator, which effects the changes in amplitude, (10): a modulated source signal (target-modified signal), (11): a multiplicator (feedback correction to the modulation), which fits the modulation to the respective feedback, (12): a modulation signal which represents the "information" carried by the carrier wave (preferably at 13.56 MHz), (13): an input of the signal, or modulation signal-generator, which is configured and/or adapted to use the phase information of the measured homeostatic signal (19) and provides the modulation signal, (14): optionally, a signal checking unit (power/current sensor), which senses the signal-amplitude for control purposes, (15): optionally, a comparator to a reference signal ($P_a(t)$), which controls the signal by comparison to the reference, (16): optionally, a reference signal ($P_a(t)$), as a stable signal for fixing signal levels, (17): a load or the target area is in general the body part of the target exposed to the radiofrequency waves.

(18): a RF-ground, a ground level not necessarily identical with the general ground (earth-potential). This ground is modified by the respective potential distribution of the RF signal as a function of its wavelength.

(19): measured homeostatic signal (like ECG, EEG, EMG, signal of the membrane ion-channels, or a signal generated starting from the morphology of a tissue etc.) The measured homeostatic signal (19) provides phase information of a systemic homeostatic signal of the target, for example when ECG or EEG is measured, or provides phase information of local homeostatic signal of the target, when the signal (19) is generated starting from the morphology of a tissue (healthy tissue or cancerous tissue). Preferably, signal (19) is preferably measured, before the treatment with the radiofrequency hyperthermia device according to the present invention, or in case signal (19) is a systemic homeostatic signal, it can be measured before and during the treatment.

The following description of the operation of the inventive device is based on the block diagram of the operation of the device provided in FIGS. 12 and 13. FIGS. 12 and 13 show both the main (power) circuit required for any RF hyperthermia treatment, including conventional hyperthermia treatment, and the additional modulation circuit(s) required by the inventive device.

The present invention relates also to a radiofrequency hyperthermia device for personalized treatment, personalized prophylaxis and personalized diagnosis using capacitive coupling in a condenser arrangement comprising a radiofrequency source (1), an amplifier (2), a sensor (3), a modulator (9) and a modulation signal input/generator (13), wherein the radiofrequency source produces a source signal (8), which is modulated by the modulator (9) using the modulation signal (12) to generate a modulated source signal (10), the modulated source signal (10) is amplified by the amplifier (2) to generate a amplified modulated signal (4) that is directed to a target area (17), and the sensor (3) detects the phase information generated by homeostasis of the target area (17) and compares the phase information with the previously obtained phase information to provide a feedback signal (5), wherein the modulation signal (12) is generated by the modulation signal input/generator (13) from the feedback signal (5) by modulating the feedback signal (5), wherein the modulation signal input/generator (13) is adapted to use the phase information of the measured homeostatic signal (19).

This radiofrequency (RF) hyperthermia device is designed for affecting homeostasis in a way to bring the fluctuations of homeostasis into a range of the target, when the target was in a healthy state.

In a preferred embodiment of the present invention, the sensor (3) is configured and/or adapted to compare the phase information obtained at time $T_{n+1}$ with the phase information detected by sensor (3) at time $T_n$, with n>0. As used herein Tn refers to a time point $T_n$ when the phase information is detected by sensor (3), which differs from time point $T_{n+1}$ by a defined time interval. For example, if the time interval is defined as being 1 minute, and n is 4, then $T_n$ is 4 minutes and Tn+1 is 5 minutes. This means that $T_n$ is the time point when the $n^{th}$ detection of the phase information by sensor (3) according to a defined interval occurs.

Preferably, sensor (3) is situated between the amplifier (2) and the target area (17) or between the target area (17) and the feedback amplifier (6).

In a further preferred embodiment according to the present invention, sensor (3) configured and/or adapted to compare the phase information obtained at time $T_{n+1}$ with the phase information detected by sensor (3) at time $T_n$, or in other words to detect the phase information generated by homeostasis of the target area (17) and to compare the phase information with the previously obtained phase information to provide a feedback signal (5), stores the following algorithm $$f(t) = inverseFourier\left(\frac{|A|e^{j\phi(\omega)}}{\sqrt{\omega}}\right)$$

wherein
φ(ω) is an arbitrary function,
φ is the phase of the amplitude, and
A is amplitude.

This algorithm is stored in sensor (3) for providing the feedback signal (5).

Also in this embodiment the presence of the feedback amplifier (6) is preferred, but not necessarily required if the feedback signal is strong enough and does not need to be amplified.

The modulated source signal (10), as well as the amplified modulated source signal (4) is applied to the target by capacitive coupling and not by radiation or radiative coupling. The capacitive coupling is done between at least two conductive electrodes, i.e. at least one electrode and at least one counter-electrode, forcing RF-current between them. That means, the RF current runs between the at least two conductive electrodes. Thus, the device of the present invention uses conduction between the opposing electrode pair and does not use radiation between the electrodes forming the antenna. Therefore, the radiofrequency hyperthermia device uses capacitive coupling in a condenser arrangement wherein the target area (17) is the dielectric material.

Thus the RF hyperthermia device of the present invention uses capacitive coupling in a condenser arrangement, wherein the target is the dielectricum, alternating current (AC) and radio frequency (RF) waves.

In contrast the state of the art RF hyperthermia devices uses radiative coupling in an antenna arrangement and apply locally heat in order to destroy tissue by burning thus causing vehement necrosis.

The inventive RF hyperthermia device uses the RF field in order to obtain phase information on the current homeostasis in order to detect any disequilibrium or maladjustment, which is the symptom of a disease and to cure the disease by bringing homeostasis of the target into a stage of homeostasis when the target was in healthy conditions.

Moreover, the present invention relates to a RF hyperthermia device comprising a modulation signal input/generator (13), which generates modulation signal (12) by modulating the feedback signal (5) or the amplified feedback signal (7) and is configured and/or adapted to use the phase information of the measured homeostatic signal (19). Moreover it is preferred that at least one of the equations (16), (17), (22), (23), (24), (25), (26), and (27) is stored in the modulation signal input/generator (13) in order to perform the modulation and/or to provide the modulation signal (12). Furthermore it is also preferred that instead of the algorithm (27) or in addition to the algorithm (27) at least one of the equations (16), (17), (22), (23), (24), (25), and (26) is stored in the sensor (3) in order to provide the feedback signal (5).

Thus, the present invention relates also to the use of a modulation signal input/generator (13), which is configured and/or adapted to use the phase information of the measured homeostatic signal (19) for the manufacture of a RF hyperthermia device for the treatment and after-treatment of tumors, cancer pain and diseases of the central nervous system.

Preferably, modulator (9) according to the present invention is configured and/or adapted to modulate the amplitude and frequency spectrum of the source signal (8) on the basis of the phase information of the measured homeostatic signal (19) and the phase information generated by homeostasis of the target area (17), wherein the source signal (8) is modulated in a way that the selectivity for the target tissue is increased, so that selectively the target tissue and not the surrounding healthy tissue is warmed-up or heated to up. Thus, the modulator (9) has to be manufactured in a way that the modulator (9) is able to modulate the amplitude and frequency spectrum of the source signal (8) by the modulation signal (12). The modulation signal (12) contains the phase information of the measured homeostatic signal (19) in a preferred embodiment.

The preferred frequency for use in the present invention is in the range of all the frequencies which are able to modulate the carrier frequency, usually up to a tenth of the carrier frequency. Most preferred is the audio range of 5-20,000 Hz because the resonance effects of biosystems lie in the audio range.

The preferred power for use in the present invention is in the range of 30 to 1500 W. Most preferred is the range of 60-250 W. This range is particularly safe and provides enough power for heating up the lesion. Tumor size (in the case of large tumors) does not exceed 1 liter in volume. For heating it up from body temperature to 40-45° C. (with a gradient of less than 10° C. per hour) even 250 W would be too much. This is only a provision for the case of high vascularisation in the tumor which may lead to a significant blood-cooling effect.

The RF hyperthermia device of the present invention is especially useful for the treatment and after-treatment of tumours, cancer, metastases and carcinomas as well as pain and diseases of the central nervous system.

The hyperthermia device of the present invention can be used to selectively treat a localised target site, wherein the localised target site is selected from tumour tissues and muscle tissue, or organs, such as for example liver, lung, heart, kidney, spleen, brain, ovary, uterus, prostate, pancreas, larynx, the gastrointestinal tract, and the gynecological tract.

The tumour tissue can be selected from adenocarcinoma, choroidal melanoma, acute leukemia, acoustic neurinoma, ampullary carcinoma, anal carcinoma, astrocytoma, basal cell carcinoma, pancreatic cancer, desmoid tumour, bladder cancer, bronchial carcinoma, non-small cell lung cancer (NSCLC), breast cancer, Burkitt's lymphoma, corpus cancer, CUP-syndrome (carcinoma of unknown primary), colorectal cancer, small intestine cancer, small intestinal tumours, ovarian cancer, endometrial carcinoma, ependymoma, epithelial cancer types, Ewing's tumours, gastrointestinal tumours, gastric cancer, gallbladder cancer, gall bladder carcinomas, uterine cancer, cervical cancer, cervix, glioblastomas, gynecologic tumours, ear, nose and throat tumours, hematologic neoplasias, hairy cell leukemia, urethral cancer, skin cancer, skin testis cancer, brain tumours (gliomas), brain metastases, testicle cancer, hypophysis tumour, carcinoids, Kaposi's sarcoma, laryngeal cancer, germ cell tumour, bone cancer, colorectal carcinoma, head and neck tumours (tumours of the ear, nose and throat area), colon carcinoma, craniopharyngiomas, oral cancer (cancer in the mouth area and on lips), cancer of the central nervous system, liver cancer, liver metastases, leukemia, eyelid tumor, lung cancer, lymph node cancer (Hodgkin's/Non-Hodgkin's), lymphomas, stomach cancer, malignant melanoma, malignant neoplasia, malignant tumours gastrointestinal tract, breast carcinoma, rectal cancer, medulloblastomas, melanoma, meningiomas, Hodgkin's disease, mycosis fungoides, nasal cancer, neurinoma, neuroblastoma, kidney cancer, renal cell carcinomas, non-Hodgkin's lymphomas, oligodendroglioma, esophageal carcinoma, osteolytic carcinomas and osteoplastic carcinomas, osteosarcomas, ovarian carcinoma, pancreatic carcinoma, penile cancer, plasmocytoma, squamous cell carcinoma of the head and neck (SCCHN), prostate cancer, pharyngeal cancer, rectal carcinoma, retinoblastoma, vaginal cancer, thyroid carcinoma, Schneeberger disease, esophageal cancer, spinaliomas, T-cell lymphoma (mycosis fungoides), thymoma, tube carcinoma, eye tumours, urethral cancer, urologic tumours, urothelial carcinoma, vulva cancer, wart appearance, soft tissue tumours, soft tissue sarcoma, Wilm's tumour, cervical carcinoma and tongue cancer. Particularly suitable for treatment are, for example, astrocytomas, glioblastomas, pancreatic cancer, bronchial cancer, breast cancer, colorectal cancer, ovarian cancer, gastric cancer, laryngeal cancer, malignant melanoma, oesophageal cancer, cervical cancer, liver cancer, bladder cancer, and renal cell cancer The hyperthermia device of the present invention can be used in combination with chemotherapy treatment with cytostatic and/or cytotoxic drugs. Example of some cytostatic and/or cytotoxic drugs are actinomycin D, aminoglutethimide, amsacrin, anastrozol, antagonists of purine and pyrimidine bases, anthracycline, aromatase inhibitors, asparaginase, antiestrogenes, bexaroten, bleomycin, buselerin, busulfan, camptothecin derivates, capecitabin, carboplatin, carmustine, chlorambucil, cisplatin, cladribin, cyclophosphamide, cytarabin, cytosinarabinoside, alkylating cytostatics, dacarbacin, dactinomycin, daunorubicin, docetaxel, doxorubicin (adriamycin), doxorubicin lipo, epirubicin, estramustine, etoposid, exemestan, fludarabin, fluorouracil, folic acid antagonists, formestan, gemcitabin, glucocorticoides, goselerin, hormones and hormone antagonists, hycamtin, hydroxy urea, idarubicin, ifosfamid, imatinib, irinotecan, letrozol, leuprorelin, lomustin, melphalan, mercaptopurine, methotrexate, miltefosin, mitomycine, mitosis inhibitors, mitoxantron, nimustine, oxaliplatin, paclitaxel, pentostatin, procarbacin, tamoxifen, temozolomid, teniposid, testolacton, thiotepa, thioguanine, topoisomerase inhibitors, topotecan, treosulfan, tretinoin, triptorelin, trofosfamide, vinblastine, vincristine, vindesine, vinorelbine, antibiotics with cytotoxic activities. All present and future cytostatics or other medicaments including gene therapy could be applied.

The treatment, after-treatment and/or prophylaxis of pain or the medical indication pain comprises pain caused by cancer, tumor associated pains, chronic pain and chronic pain conditions, head pains, migraine, migraine headache, neuralgias, trigeminal neuralgia, post-therapeutic neuralgia, neuropathic pains, persistent musculoskeletal pains and persistent visceral pains.

The indications persistent musculoskeletal pains and persistent visceral pains further comprise persistent back pains, persistent neck pains, persistent shoulder pains, persistent joint pains and fibromyalgia.

The pain which can be treated by the present inventive device can be caused and/or associated with cancer, tumors, the premenstrual syndrome, mastalgia, stomach pain associated with irritable colon and pains associated with carcinoid syndrome.

If a pain event lasts for more than three to six months, it is referred to as chronic pain. Causes thereof may be incurable diseases such as malignant tumors or rheumatic diseases. However, the connection between the pain and the disorder or respectively the disease which originally caused the pain is often no longer identifiable or the original disorder can no longer be remedied. Furthermore, various environmental influences like stress or weather changes can trigger or enhance the pain. A chronic manifestation of pain often includes different forms of pain.

Back pains (amongst others as a consequence of herniated discs, nerve root compression syndrome), head pains (amongst others migraine, tension-type headache, cluster headache), rheumatic pains (amongst others arthritis, fibromyalgia), neuralgias (amongst others trigeminal neuralgia, herpes zoster-induced pain), tumor associated pains (amongst others brain tumor, bone metastases), degenerative pains (amongst others osteoporosis, arthrosis) and phantom pains (amongst others after amputation, plexus lesion) are mentioned as the most frequent forms of chronic pain.

Chronic pain often last for several years or decades. Frequently, patients suffering from chronic pain develop emotional problems. Many pain patients suffer from inactivity and listlessness; they feel hopeless and desperate, complain about feelings of anxiety and depression, perceive themselves as limited in their self-esteem. Such psychic symptoms are warning signals of a chronification, just as general, nonspecific physical complaints such as intestine associated problems (diarrhea or respectively constipation), irritable bladder, dizziness, dyspnea, palpitations or a feeling of tightness in the chest.

Different mechanisms in the peripheral and central nervous systems are involved in the causation of chronic pain. The sensitization of pain fibers and their local hyperexcitability are substantial pathogenic mechanisms which are relevant as far as peripheral pain perception in the course of the causation of chronic pain conditions is concerned. Other pathomechanisms comprise the longer lasting enhancement of pain signals and a recruitment of usually silent nerve fibers in the area of the spinal cord that lead to a larger spatial extension of the pain perception. Finally, in the brain the pain potentials arriving in increased number from the periphery lead to changes in signal transmission in terms of an enhancement of the pain perception and a long-term change in pain processing.

Even when lasting only for a few minutes, intensive pain stimuli can lead to persistent structural and functional changes which intensify the transmission and the processing of pain stimuli. These procedures are similar to cellular activities such as those that can be observed in all more complex, neuronal learning processes; consequently, it is analogously referred to as pain memory. In said context, the term pain memory includes the ability of the nervous system to generate a memory trace for an occurred painful stimulation through the whole pain processing system.

Thus, another aspect of the present invention is the use of the inventive hyperthermia device to provide an improved method of hyperthermia treatment for pain management. In these cases the treatment could be carried out at normal body temperature or at least so that the temperature increase in the target tissue is negligible.

When used for treatment of inflammatory conditions the RF hyperthermia device of the present invention can be used in combination with an anti-inflammatory drug treatment such as a non-steroidal anti-inflammatory drug (NSAID), for example, alcofenac, aceclofenac, sulindac, tolmetin, etodolac, fenopren, thiaprofenic acid, meclofenamic acid, meloxicam, tenoxicam, lornoxicam, nabumetone, acetaminophen, phenacetin, ethenzamide, sulpyrine, mefanamic acid, flufenamic acid, diclofenac sodium, loxoprofen sodium, phenylbutazone, indomethacin, ibuprofen, ketoprofen, naproxen, oxaprozin, flurbiprofen, fenbufen, pranoprofen, floctafenine, piroxicam, epirizole, tiaramide hydrochloride, zaltoprofen, gabexate mesilate, camostat mesilate, ulinastatin, colchicine, probenecid, sulfinpyrazone, benzbromarone, allopurinol, salicylic acid, atropine, scopolamine, levorphanol, ketorolac, tebufelone, tenidap, clofezone, oxyphenbutazone, prexazone, apazone, benzydamine, bucolome, cinchopen, clonixin, ditrazol, epirizole, fenoprofen, floctafenin, glaphenine, indoprofen, niflumic acid and suprofen, or with a steroidal anti-inflammatory drugs, for example, dexamethasone, hexestrol, methimazole, betamethasone, triamcinolone, fluocinonide, prednisolone, methylprednisolone, hydrocortisone, fluorometholone, beclomethasone dipropionate, estriol, clobetasol, diflorasone diacetate, halbetosal propionate, amicinonide, desoximetasone, halcinonide, mometasone furoate, fluticasone propionate, flurandrenolide, clocortalone, predincarbate, aclometasone dipropionate and desonide.

Another aspect of the present invention is the use of the inventive RF hyperthermia device to provide an improved method of hyperthermia treatment for upper respiratory tract disease. Upper respiratory tract infections are caused by viruses and bacteria that have an optimum growth and survival temperature lower than the core body temperature. Therefore these infections can also be treated using hyperthermia therapy. For example, in bacterial infections of the upper part of the respiratory system (e.g. a common cold) the positive effect of heat application is well-known. The mucosa is highly conductive. Similar as in tumor tissue the heat effect is also concentrated (as in asthma treatment). Consequently, the inventive method is higher selective for a common cold than other heating techniques. Thus the hyperthermia device of the present invention is also useful for the treatment of rhinitis and other upper respiratory tract infections. Examples of viruses that cause upper respiratory tract infections are rhinoviruses, coronaviruses, adenoviruses, myxoviruses, coxsackie viruses, echoviruses, parainfluenza viruses, respiratory syncytial virus and influenza viruses. Examples of bacteria that cause upper respiratory tract infections are *Mycoplasma pneumoniae, Chlamydia pneumoniae, Streptococcus pneumoniae, Corynebacterium diptheriae*, and *Haemophilus influenzae*.

Still another aspect of the present invention is a method for modulating a signal of a radiofrequency device comprising a radiofrequency source (1), which provides a source signal (8), an amplifier (2), a sensor (3), a feedback amplifier (6), a modulator (9) and a modulation signal input/generator (13), comprising the steps of modulating the source signal (8) by modulator (9) using the modulation signal (12) to generate a modulated source signal (10), amplifying the modulated source signal (10) with the amplifier (2) to generate amplified modulated signal (4), directing the amplified modulated signal (4) to a target area (17), detecting the phase information generated by homeostasis of the target area (17) and comparing the phase information with the previously obtained phase information to provide a feedback signal (5), modulating the feedback signal (5) by the modulation signal input/generator (13) using the phase information of the measured homeostatic signal (19).

In other words, the present invention relates to method for modulating a signal of a radiofrequency device comprising a radiofrequency source (1), which provides a source signal (8), an amplifier (2), a sensor (3), a feedback amplifier (6), a modulator (9) and a modulation signal input/generator (13), comprising the steps of modulating the source signal (8) by modulator (9) using the modulation signal (12) to generate a modulated source signal (10), amplifying the modulated source signal (10) with the amplifier (2) to generate amplified modulated signal (4), directing the amplified modulated signal (4) to a target area (17), using the difference in the phase-code of the phase of the power-amplitudes of the power-density function of the fluctuation of the homeostatic equilibrium of the target area (17) and comparing the phase information with the previously obtained phase information to provide a feedback signal (5), modulating the feedback signal (5) by the modulation signal input/generator (13) using the phase information of the measured homeostatic signal (19).

Thus, the present invention provides a method for modulating a signal of a radiofrequency device comprising a radiofrequency source (1), which provides a source signal (8), an amplifier (2), a sensor (3), a feedback amplifier (6), a modulator (9) and a modulation signal input/generator (13), comprising the steps of modulating the source signal (8) by modulator (9) using the modulation signal (12) to generate a modulated source signal (10), amplifying the modulated source signal (10) with the amplifier (2) to generate amplified modulated signal (4), directing the amplified modulated signal (4) to a target area (17), detecting the changes of the phase-code of the phase of the power-amplitudes of the power-density function of the fluctuation of the homeostatic equilibrium of the target area (17) and comparing the phase information with the previously obtained phase information to provide a feedback signal (5), modulating the feedback signal (5) by the modulation signal input/generator (13) using the phase information of the measured homeostatic signal (19).

Since these methods are performed and carried out by using the inventive RF hyperthermia device, these methods are also personalized so that one can speak about personalized methods.

DESCRIPTION OF THE FIGURES

FIG. 9: Constructions of a Hilbert fractal in space FIG. 10: Music from space-fractal by the "post-modern" pianola. The paper-cylinder of pianola coding the fractal and makes possible to play it as music.

FIG. 11: The discrete phase-function of the time-transformed Hilbert-fractal

FIG. 14: shows how a fractal-structure can be transformed to the corresponding time-fractal structure, as alternative for generation a homeostatic signal starting from the morphology of a tissue.

Figure 1:
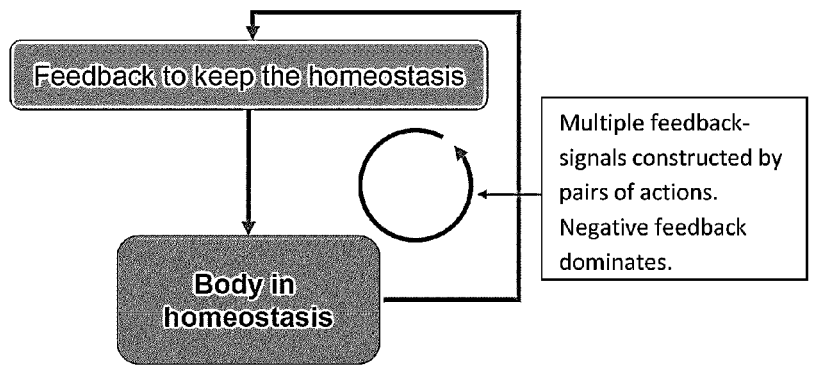
FIG. 1: The natural healthy state is stabilized by the negative feedback loops (arrow) of physiology
Figure 2:
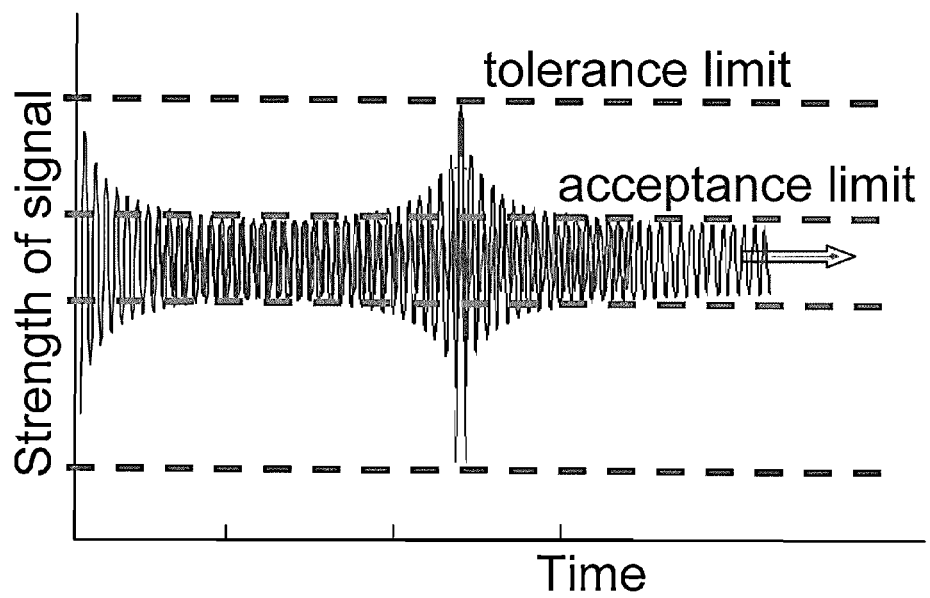
FIG. 2: The fluctuations must be in the definite range properly keeping the control. Consequently, the average always has to be fixed in time, and the random fluctuations remain in the band for a long-range of the time.
Figure 3:
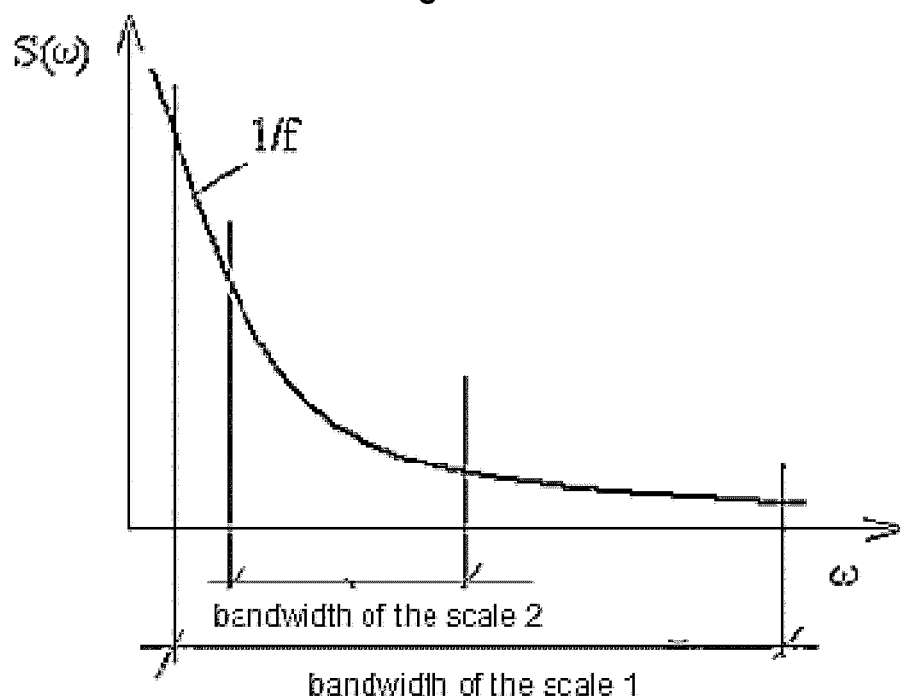
FIG. 3: Narrowing the bandwidth by scaling
Figure 4:
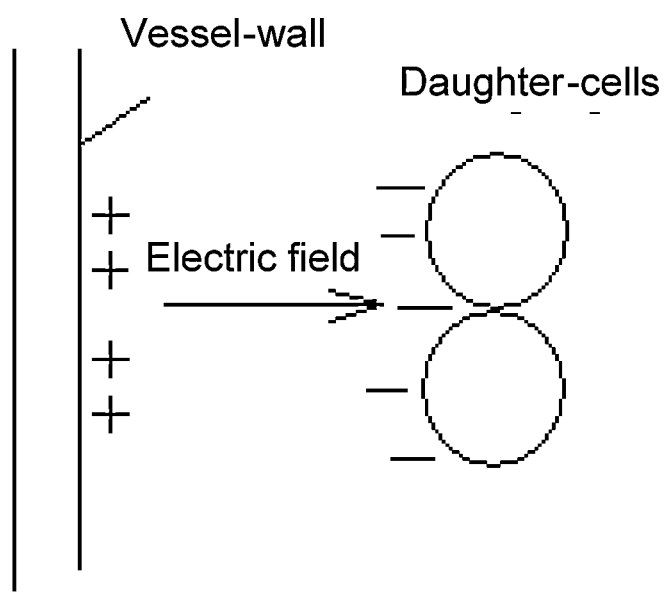
FIG. 4: Construction of electric potential gradient by angiogenesis
Figure 5:
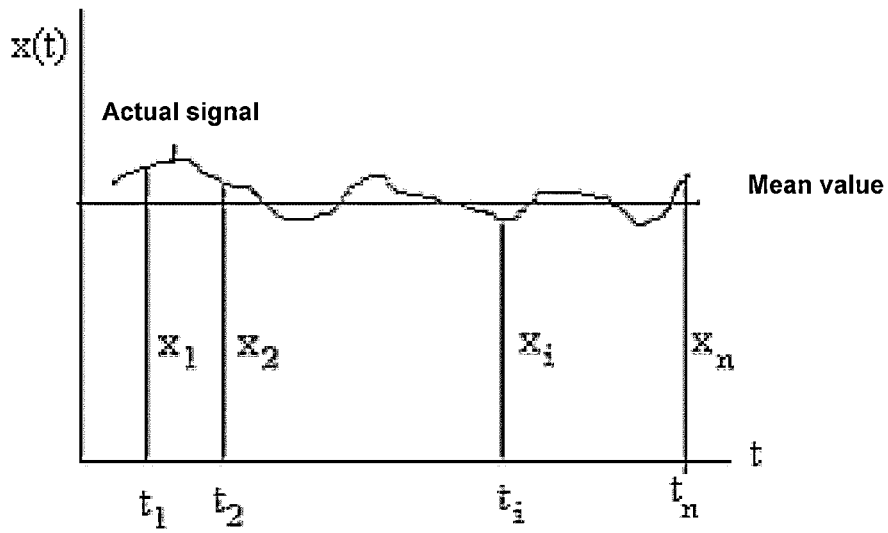
FIG. 5: Homeostasis controlled parameter of the environmental signal
Figure 6:
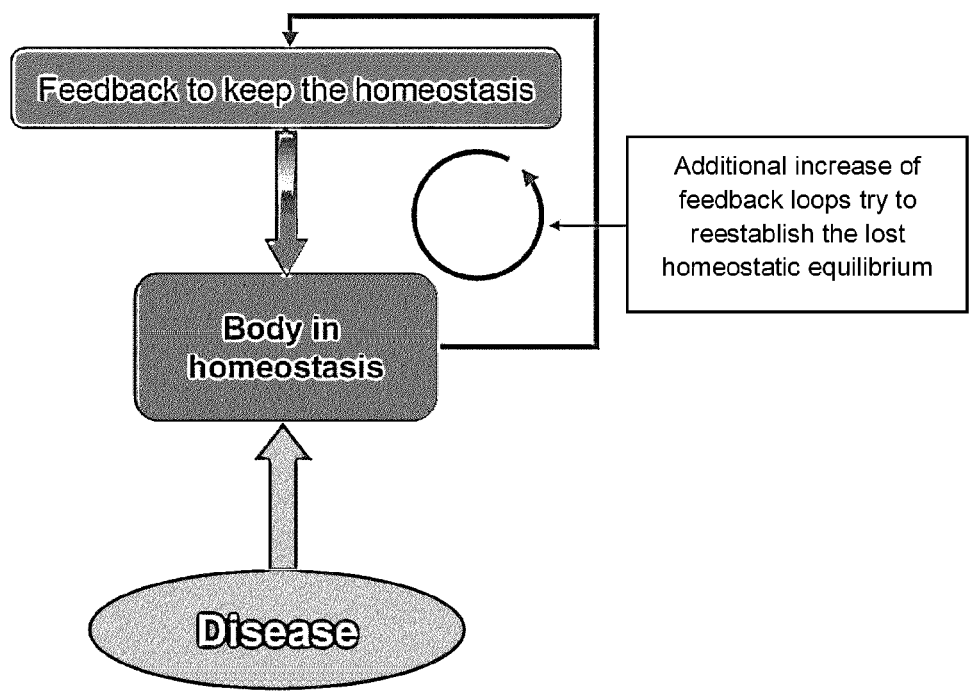
FIG. 6: The disease breaks the homeostasis, so the physiology tries to compensate and correct the damage
Figure 7:
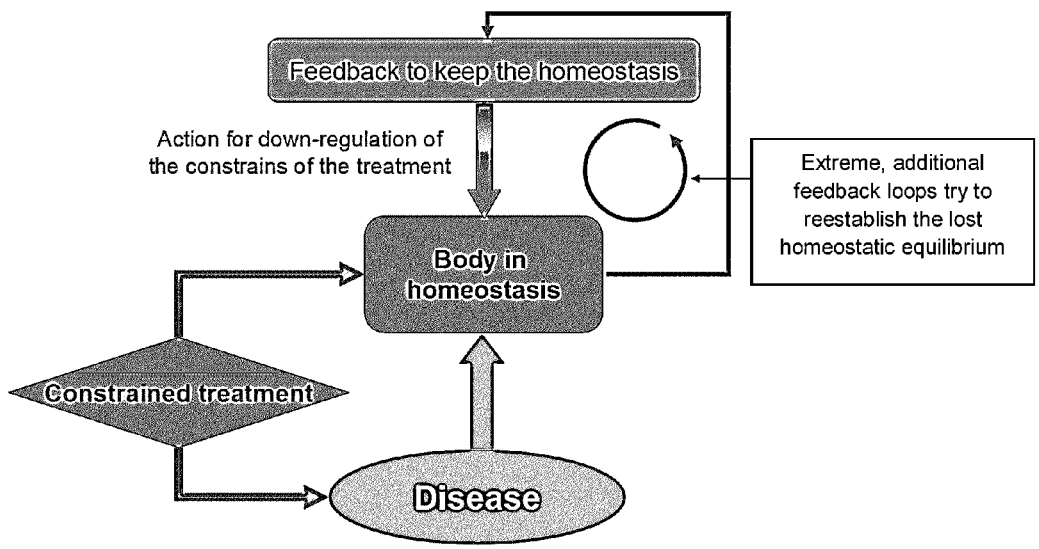
FIG. 7: The classical hyperthermia introduces a new constrained effect which induces even more physiological feedback, forcing the body for the "double front" fighting
Figure 8:
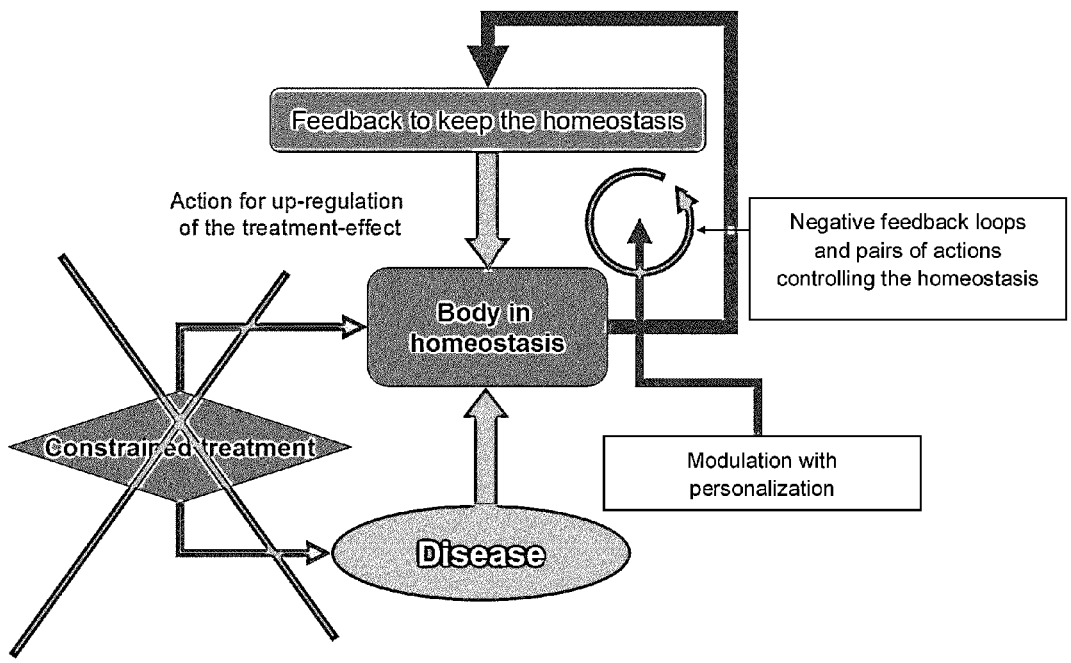
FIG. 8: Modulation acts differently. It helps the natural feedback loops for natural corrections
Figure 12:
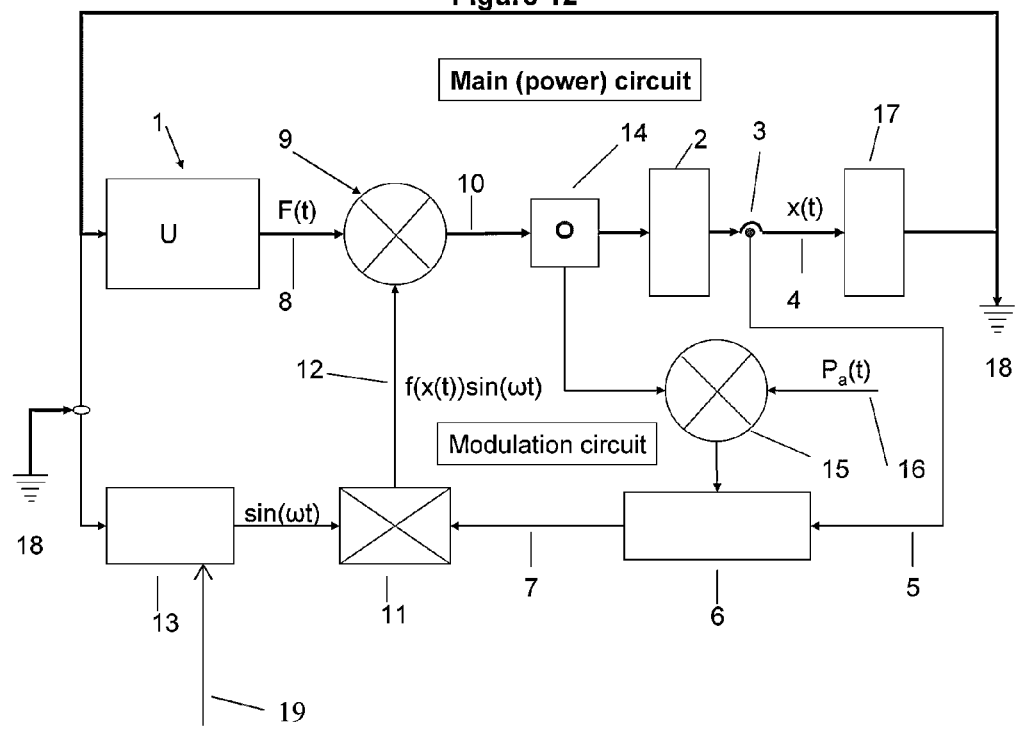
FIG. 12: shows a possible arrangement of an RF hyperthermia device of the present invention.
Figure 13:
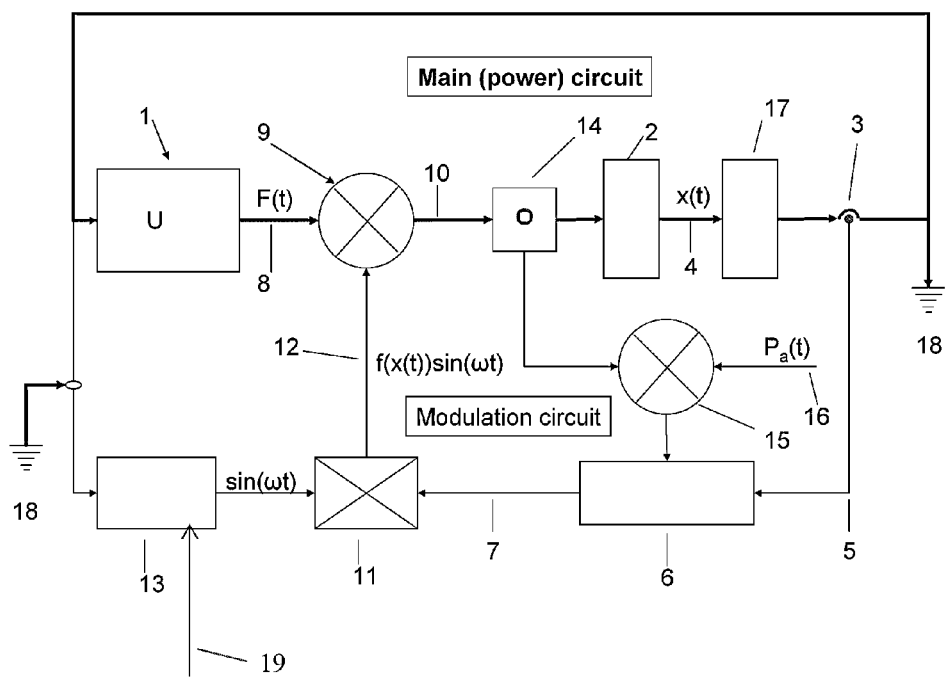
FIG. 13: shows another possible arrangement of an RF hyperthermia device of the present invention.

The invention claimed is:

1. A radiofrequency hyperthermia device for personalized treatment, personalized prophylaxis and personalized diagnosis using capacitive coupling comprising:
    a radiofrequency source for producing a source signal;
    a modulator for modulating the source signal to generate a modulated source signal;
    an amplifier for amplifying the modulated source signal to generate an amplified modulated signal that is directed to a target area;
    a sensor for detecting a phase information of a signal generated by homeostasis of a target area; and
    a modulation signal input/generator for generating a modulation signal using said phase information of a measured homeostatic signal,
    wherein the measured homeostatic signal is ECG, EEG, EMG, signal of the membrane ion-channels, or a signal generated starting from the morphology of a tissue of the target area.

2. The radiofrequency hyperthermia device according to claim 1, wherein sensor (3) is configured to compare the phase information obtained at time $T_{n+1}$ with a previously obtained phase information at time $T_n$ to provide a feedback signal, and wherein n>0.

3. The radiofrequency hyperthermia device of claim 2, further comprising a multiplicator for fitting the modulation signal to the feedback signal.

4. The radiofrequency hyperthermia device of claim 2, further comprising a feedback amplifier for amplifying the feedback signal.

5. The radiofrequency hyperthermia device of claim 4, wherein the sensor is situated between the target area and the feedback amplifier.

6. The radiofrequency hyperthermia device of claim 1, wherein the modulation signal input/generator comprises a multiplicator and/or a feedback amplifier.

7. The radiofrequency hyperthermia device of claim 1, wherein the sensor is situated between the amplifier and the target area.

8. The radiofrequency device of claim 1, wherein the radiofrequency hyperthermia device uses capacitive coupling in a condenser arrangement wherein the target area is a dielectric material.

9. The radiofrequency device of claim 1, wherein the modulator is configured to modulate an amplitude and a frequency spectrum of the source signal on the basis of the phase information of the measured homeostatic signal and the phase information generated by homeostasis of the target area.

10. The radiofrequency device of claim 2, wherein an algorithm for providing the feedback signal is stored in the sensor, wherein the algorithm is $$f(t) = inverseFourier\left(\frac{|A|e^{j\phi(\omega)}}{\sqrt{\omega}}\right),$$

wherein $\varphi(\omega)$ is an arbitrary function, $\varphi$ is the phase of the amplitude, and A is the amplitude.

11. A method for personalized treatment, after-treatment, prophylaxis, prevention of relapse or diagnosis of tumours, cancer, metastases, carcinomas, pain, migraine, or diseases of the central nervous system comprising exposing a target area to an amplified modulated signal from a radiofrequency hyperthermia device of claim 1.

12. A method for personalized treatment, after-treatment, prophylaxis, prevention of relapse or diagnosis of tumours, cancer, metastases, carcinomas, pain, migraine, or diseases of the central nervous system comprising exposing a target area to an amplified modulated signal from a radiofrequency hyperthermia device,
    wherein the amplified modulated signal is obtained from a source signal generated by a radiofrequency source, modulated by a modulation signal and amplified, wherein the modulation signal is generated from a feedback signal by modulating the feedback signal using the phase information of a measured homeostatic signal from the target area in a way that the phase information of a signal generated by homeostasis of the target area is detected at time $T_{n+1}$ and compared with a previously obtained phase information at time $T_n$,
    wherein the measured homeostatic signal is ECG, EEG, EMG, signal of the membrane ion-channels, or a signal generated starting from the morphology of a tissue of the target area.

* * * * *